United States Patent [19]

Khan et al.

[11] Patent Number: 6,049,428
[45] Date of Patent: Apr. 11, 2000

[54] DICHROIC LIGHT POLARIZERS

[75] Inventors: Ir G Khan; Yuri A. Bobrov; Leonid Y. Ignatov; Elena Y. Shishkina, all of Moscow, Russian Federation; Pavel I Lazarev, Menlo Park, Calif.; Alexey V. Kurbatov, Moscow, Russian Federation

[73] Assignee: Optiva, Inc., San Mateo, Calif.

[21] Appl. No.: 08/836,635

[22] PCT Filed: Nov. 17, 1995

[86] PCT No.: PCT/US95/14413

§ 371 Date: Aug. 4, 1997

§ 102(e) Date: Aug. 4, 1997

[87] PCT Pub. No.: WO96/16015

PCT Pub. Date: May 30, 1996

[30] Foreign Application Priority Data

Nov. 18, 1994 [RU] Russian Federation ............. 94041721
Jun. 5, 1995 [RU] Russian Federation ............. 95109284
Jul. 31, 1995 [RU] Russian Federation ............. 95113563
Oct. 6, 1995 [RU] Russian Federation ............. 95117377
Oct. 6, 1995 [RU] Russian Federation ............. 95117403

[51] Int. Cl.[7] ........................... G02B 5/30; C07D 221/22; C09B 44/10; C07C 245/00
[52] U.S. Cl. ........................... 359/491; 359/492; 546/35; 546/37; 534/607; 534/611; 534/615; 534/818; 534/781; 534/791; 534/825; 534/827
[58] Field of Search ................................... 359/491, 492; 546/35, 37; 534/607, 611, 615, 818, 827, 781, 791, 825

[56] References Cited

U.S. PATENT DOCUMENTS

| 4,133,775 | 1/1979 | Bloom | 252/300 |
| 4,440,541 | 4/1984 | Berke | 8/489 |
| 5,739,296 | 4/1998 | Gvon et al. | 534/577 |

FOREIGN PATENT DOCUMENTS

| 0 049 873 | 4/1982 | European Pat. Off. | C09B 5/28 |
| 0 557 121 | 8/1993 | European Pat. Off. | C08F 2/00 |
| WO 96/16015 | 5/1996 | WIPO | C07C 50/18 |

*Primary Examiner*—Johann Richter
*Assistant Examiner*—Joseph Murray
*Attorney, Agent, or Firm*—Skjerven, MacPherson, Franklin and Friel

[57] ABSTRACT

The present invention provides dyes of formula I–XXXIV, described in detail below, and dichroic light polarizers based on the dyes. In the dichroic light polarizers of this invention the dye molecules are aggregated into particles oriented in a predetermined direction on a surface of a substrate to enable the dye to polarize light transmitted through the dye. In another embodiment, a dichroic light polarizer includes a molecularly oriented layer of an organic dye on a surface of a substrate. The layer has a non-periodic arrangement of different polarizing elements. Each of the polarizing elements have differing orientations of the polarization vector in the substrate plane and/or differing colors. The dichroic light polarizer may contain one or more additional dye layers and may have a transparent layer intermediate to the dye layer.

21 Claims, 6 Drawing Sheets

DICHROIC LIGHT POLARIZERS

BACKGROUND OF THE INVENTION

1. Field of the Invention

The present invention relates to colored and neutral dichroic light polarizers (DLPs) based on organic dyestuffs and to processes of preparation thereof. In one embodiment, the dichroic light polarizers are adapted for demanding operation or production conditions, such as for fabrication of laminated automobile windshields, for illumination devices, and for construction and architectural purposes. In addition, the invention relates to a method for preparing a film with high polarizing efficiency at high velocity of application.

2. Description of the Related Art

Dichroic light polarizers (DLPs) can be based on the organic dyes having sulfoacids of azo or polycyclic compounds or mixtures thereof. These dyes are capable of forming lyotropic liquid crystal phases that form stable lyotropic liquid crystals and liquid crystal compositions. (See for example PCT/US94/05493, published Aug. 8, 1994.)

In addition to the dyes, these liquid crystal materials may contain certain water-soluble, low molecular organic compounds, antioxidants, inhibitors, and/or surfactants. A thin molecularly ordered dye film is formed during the deposition of the lyotropic liquid crystal materials onto a substrate surface with simultaneous mechanical orientation, and subsequent removal of solvent. This film is a polarizing coating that is capable of converting natural unpolarized light into polarized light.

The dichroic light polarizers obtained using such liquid crystal materials offer high thermal and radiation stability, and exhibit good polarization characteristics. Such dichroic light polarizers based on polarizing coatings have the following disadvantages. 1) These dichroic light polarizers have insufficient polarizing efficiency due to light scattering at the interfaces formed by the domain structure of the polarizing coating. 2) These dichroic light polarizers are based on a polarizing coating having polarization vector which is ordered only along the direction of macroscopic orientation. 3) Current preparation methods cannot provide polarizing coatings with preset distribution of the color and the orientation of polarization vector.

SUMMARY OF THE INVENTION

The present invention provides dyes of formula I–XXXIV, described in detail below and dichroic light polarizers based on the dyes. In the dichroic light polarizers of this invention, the dye molecules are aggregated into particles oriented in a predetermined direction on a surface of a substrate to enable the dye to polarize light transmitted through the dye.

In another embodiment, a dichroic light polarizer includes a molecularly oriented layer of an organic dye on a surface of a substrate. The layer has a non-periodic arrangement of different polarizing elements. Each of the polarizing elements have differing orientations of the polarization vector in the substrate plane and/or differing colors. The dichroic light polarizer may contain one or more additional dye layers and may have a transparent layer intermediate the dye layers.

Each of the additional layers contains a set of polarizing elements with different orientations of the polarization vector and/or colors. The directions of the polarization vectors in polarizing elements occurring in various layers may either coincide with or differ from each other. In another embodiment, a dichroic light polarizer includes the polarizing elements having the shape of bands with equal widths, differing by their color and having parallel or mutually perpendicular orientations of their polarization axes. A dichroic light polarizer may contain the polarizing elements of an arbitrary shape, and the polarization axes in the neighboring elements form an angle between 0 and 90° with one another.

The present invention provides also processes for the fabrication of a dichroic light polarizer by coating a substrate with a solution of an organic dye occurring in the lyotropic liquid-crystal state, with simultaneous orientation of the dye, followed by removal of the substrate. The method is distinguished by that the direction of orienting action during the dye film orientation forms an angle α of 0<α<90° with the direction of substrate motion.

DETAILED DESCRIPTION OF THE INVENTION

Figure 1D:
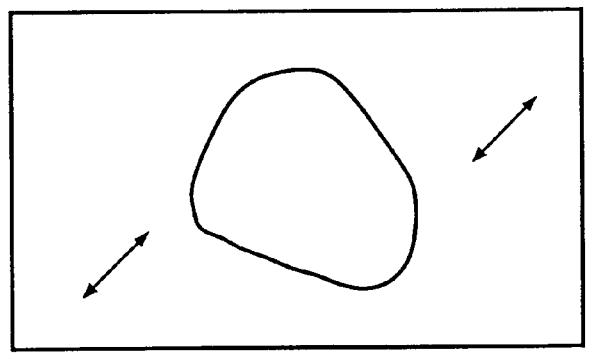
FIGS. 1(*a–h*) illustrate various embodiments of dichroic light polarizers according to the present invention.
Figure 1C:
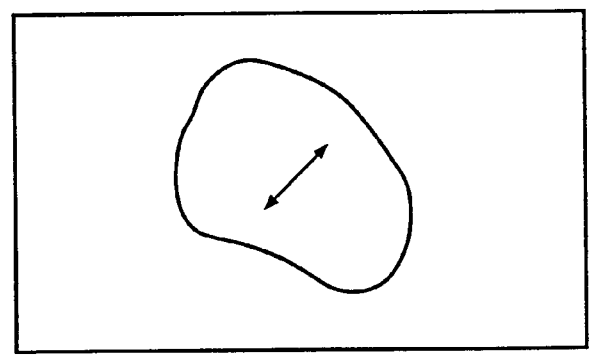

The present invention provides a liquid crystal material that can be used to produce yellow, red, green, and grey dichroic light polarizers having high polarization characteristics (e.g., with K values not less than 15). The liquid crystal materials of the present invention contain an organic dye represented by any of formulas I–XXXIV, below or mixtures thereof that are capable of forming the liquid crystal phase.

The materials also facilitate preparation of polarizing coatings with high polarizing characteristics using high velocity application methods. This is accomplished by using a dye of this invention, which dyes are able to form stable lyotropic liquid crystalline phases.

In addition to a dye of this invention, the liquid crystal materials of the present invention can include a modifying additive in a suitable solvent.

Dyes I–XXXIV

The dyes capable of forming lyotropic liquid crystals of this invention are described below. In some embodiments, the dyes represented by formulas I–XXXIV, and their mixtures are used as a film-forming component in the material for polarizing coatings. As used herein dyes of formulas I–XXXIV are as described below. Abbreviations used in the formulas are described following the description of the formulas Formula I:
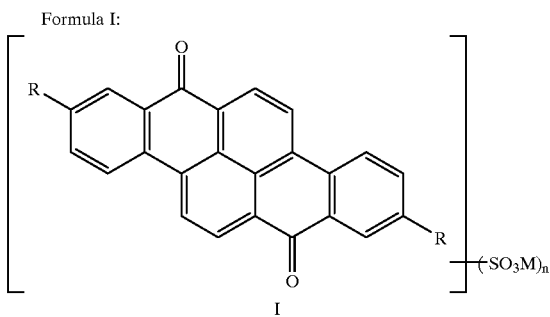
wherein R=H, Br, NHAr,
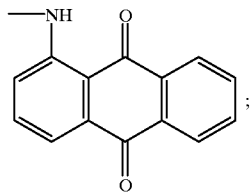
M is a cation; and
n=2–4.
Formula II:
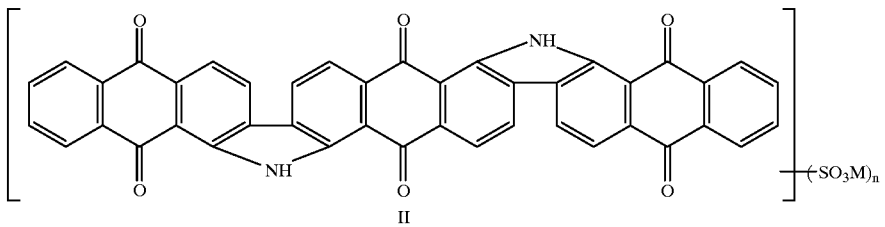
wherein M is a cation; and
n=2–4.
Formula III:
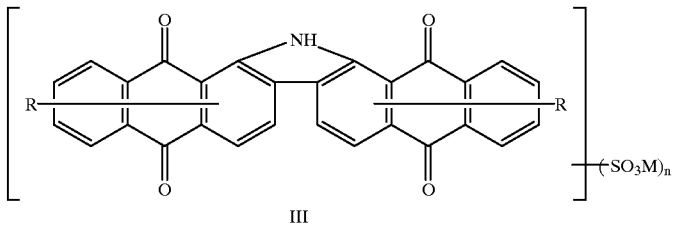
wherein R=H, NHCOPh;
M is a cation; and
n=2–4.
Formula IV:
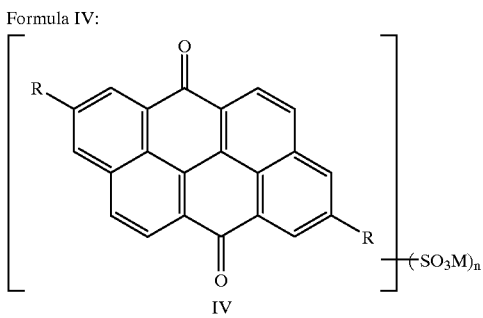

wherein R, M, and n are as in formula I.
n=2–4.
Formula V:
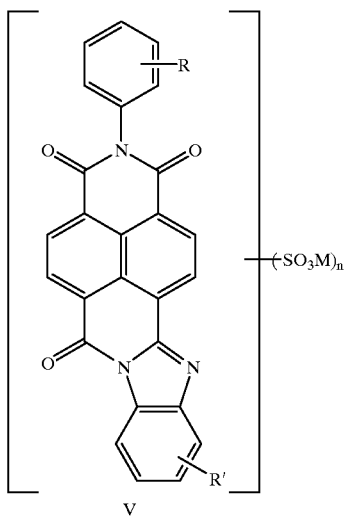
wherein R, R'=H, Hal, Alk, OAlk, ArNH, OPh;
M is a cation; and
Formula VI:
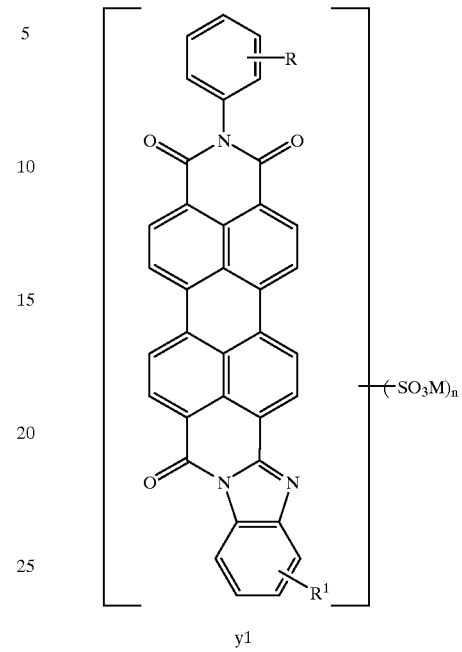
wherein R, R', M, and n are as in formula V.
Formula VII:
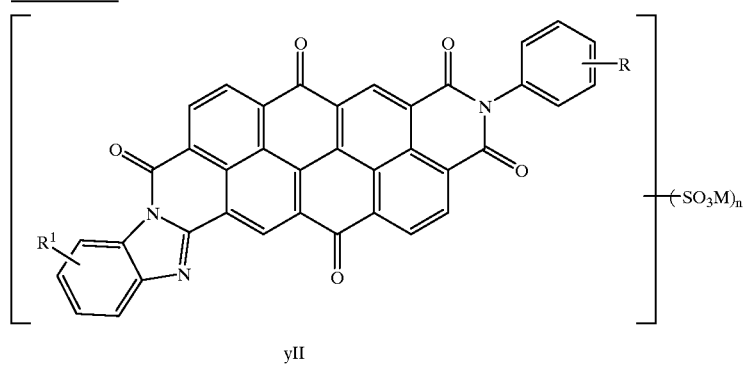
wherein R, R', M, and n are as in formula V.
Formula VIII:
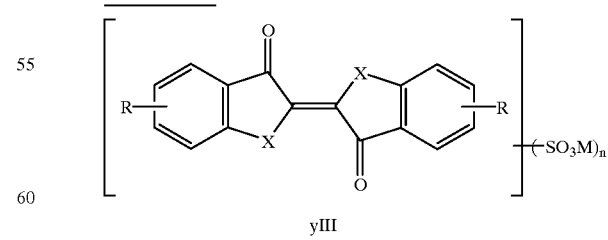

wherein X=NH, S;
R=Hal, AlkO;
M is a cation; and
n=1–3.
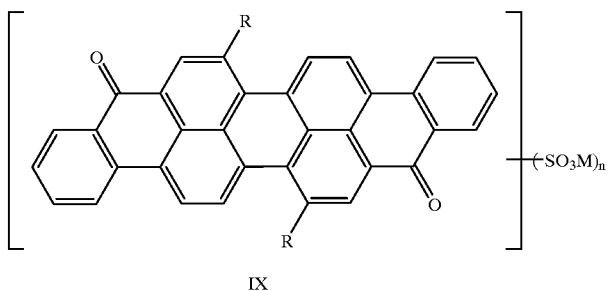
IX
wherein R=H, OH, OCH$_3$;
M is a cation; and
n=2–4.
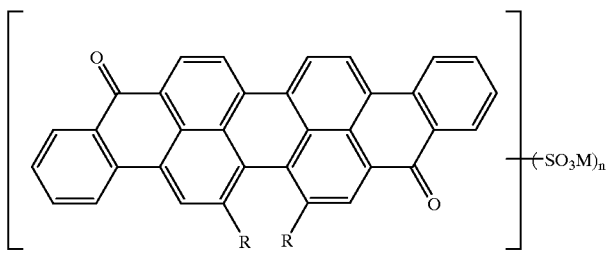
X
wherein R, M, and n are as in formula IX.
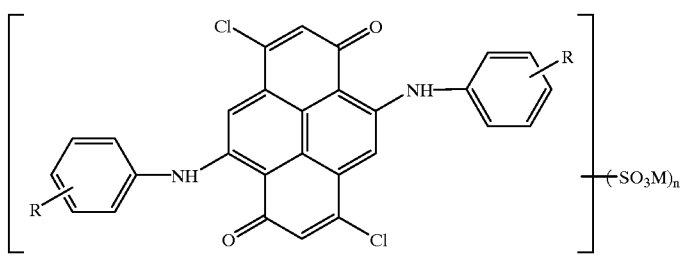
XI wherein R, M, and n are as in formula V.

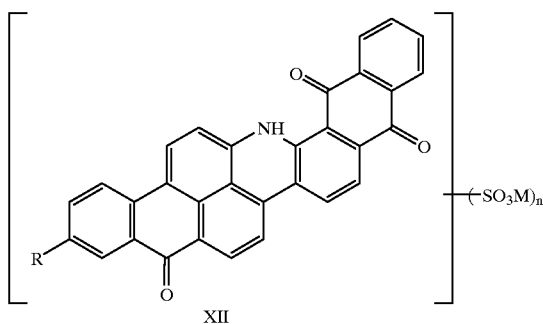

wherein R, M, and n are as in formula I.

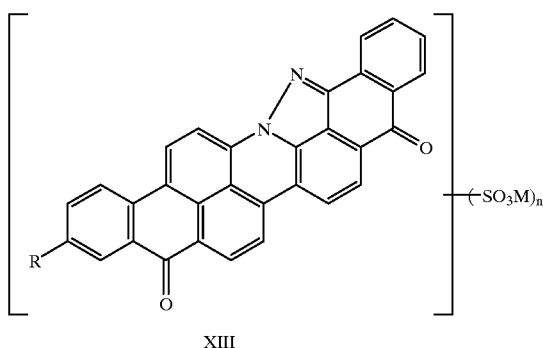

wherein R, M, and n are as in formula I.

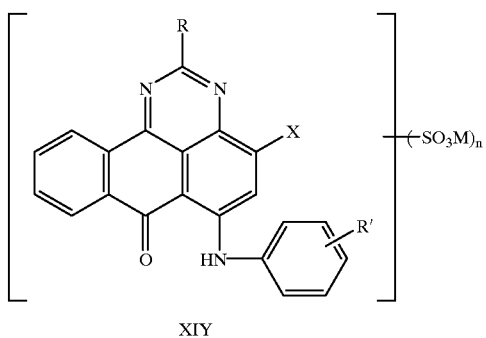

wherein X=H, Br, SO₃M;
R=H, Ar;
R'=H, Hal, Alk, OAlk, NHPh, OPh;
M is cation; and
n=2–4.

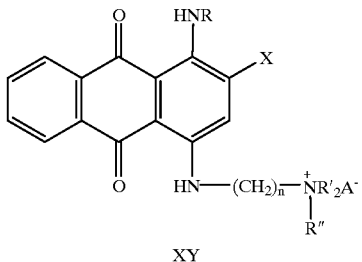

wherein X=H, Br;
R=H, Alk, Ar;
R', R"=CH$_3$, C$_2$H$_5$;
A$^-$=Hal$^-$, CH$_3$SO$_4^-$, ClO$_4^-$, BF$_4^-$; and
n=2–3.

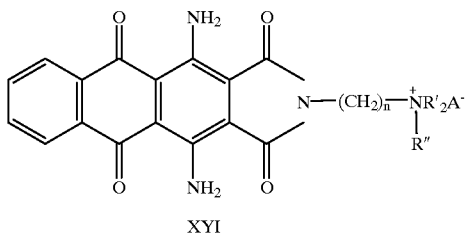

wherein R', R", A$^-$, and n are as in formula XV.

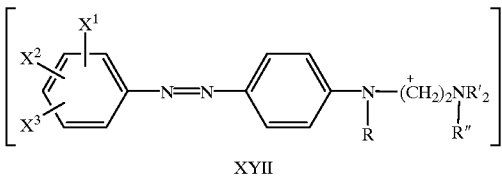

wherein R', R", and A$^-$ are as in formula XV;
R=CH$_3$, C$_2$H$_5$; and
X$^1$, X$^2$, X$^3$=H, Cl, NO$_2$, CH$_3$O.

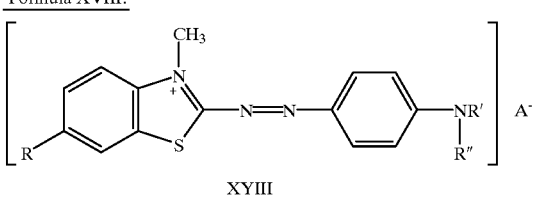

wherein R=H, CH$_3$O;
R'=CH$_3$, C$_2$H$_5$, Ar;

R"=C₂H₅, C₂H₄OH; and
A⁻ is as in formula XV.
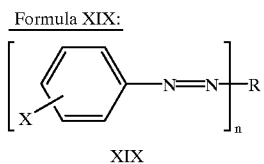
wherein X=COOM, PO(OM)₂;
n=1–2;
M is a cation;
R', R"=H, Hal;
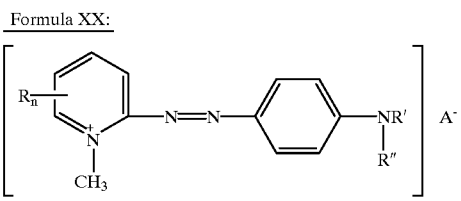
wherein R=CH₃, C₂H₅;
R'=H, Alk;
R"=Alk, Ar; and
n=0–1.
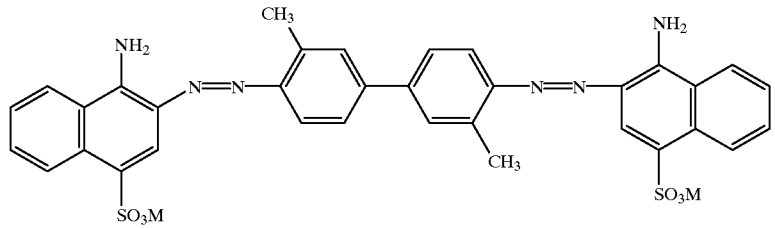
wherein M is a cation.
Y=NH₂, OM; and
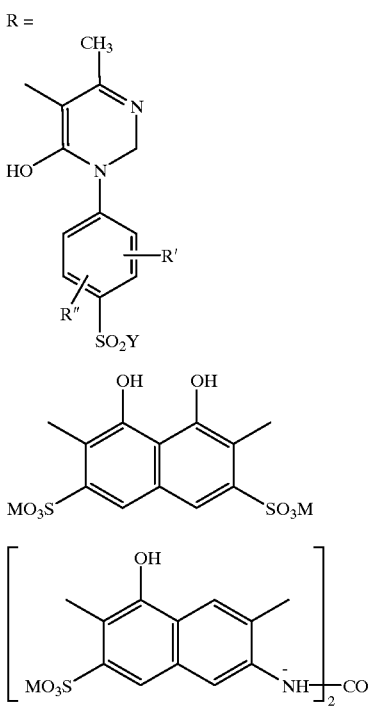
Formula XXII:
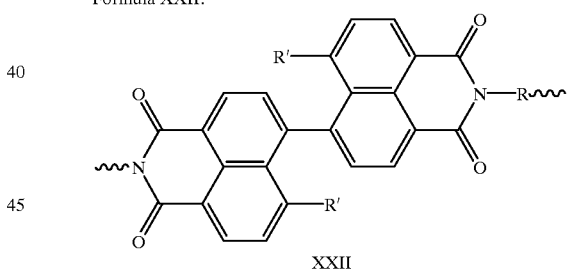
wherein
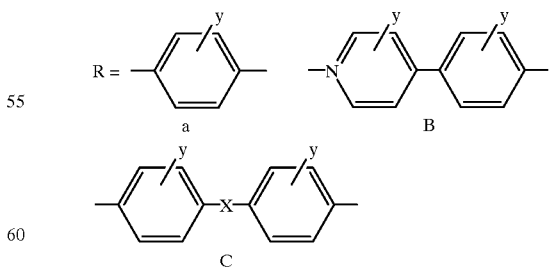
X=O, CH₂, NH, CONH, NHCONH, CH=CH;
Y=H, CH₃, CH₃O, COOM, SO₃M;
R'=H, NO₂, COOM, SO₃M; and
M is a cation.

Formula XXIII:
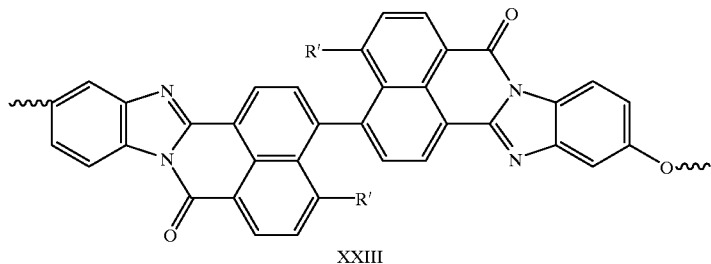
wherein R' is as in formula XXII.
Formula XXIV:
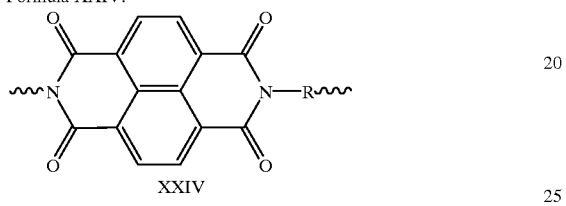
wherein R is as in formula XXII.
Formula XXV:
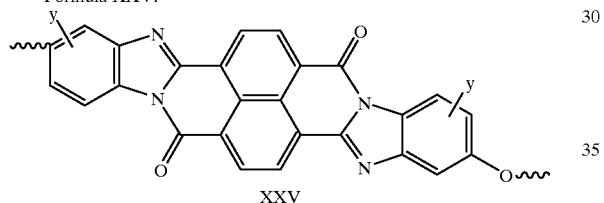
wherein Y=H, SO$_3$M; and
M is a cation.
Formula XXVI:
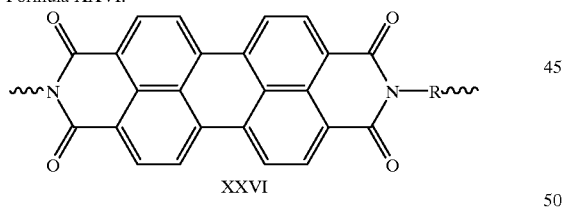
wherein R is as in formula XXII.
Formula XXVII:
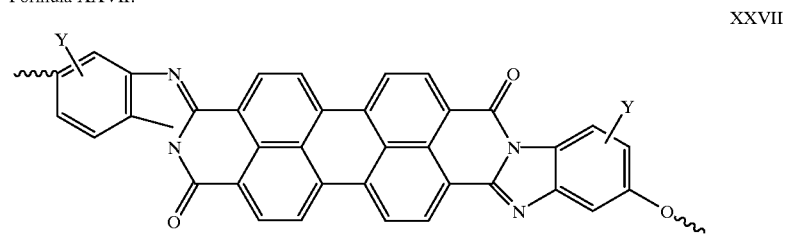

wherein Y is as in formula XXV.
Formula XXVIII:
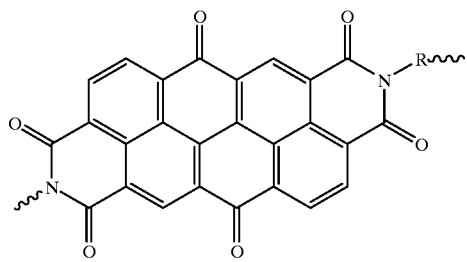
XXVIII
wherein R is as in formula XXII.
Formula XXIX:
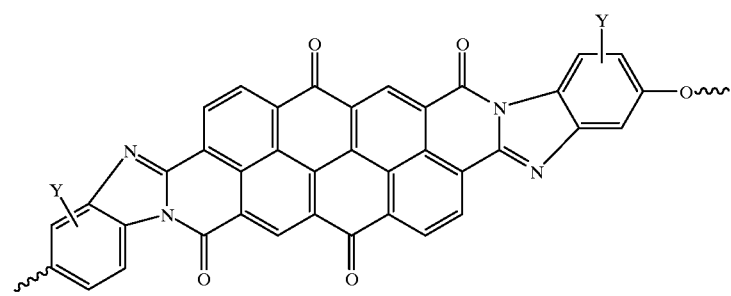
XXIX
wherein Y is as in formula XXV.
Formula XXX:
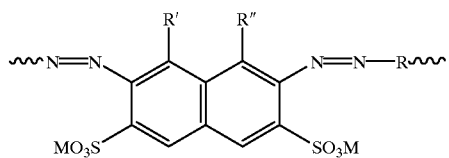
XXX
wherein R, M are as in formula XXII; and
R', R" OH, NH$_2$.
Formula XXXI:
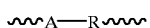
XXXI
wherein R is as in formula XXII; and
A =
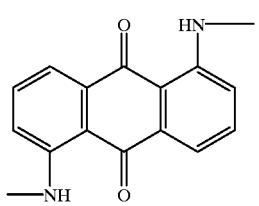
a
-continued
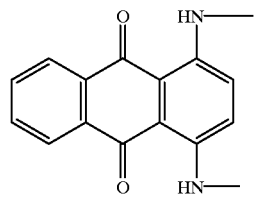
B
-continued
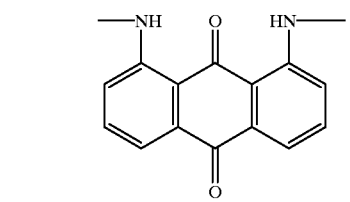
c
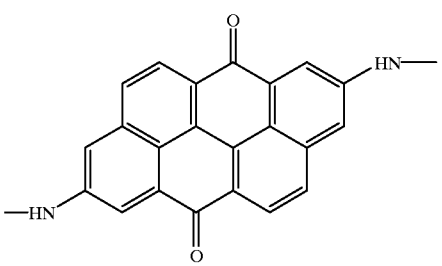
d
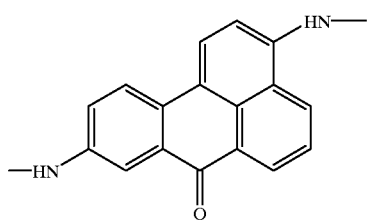
e -continued
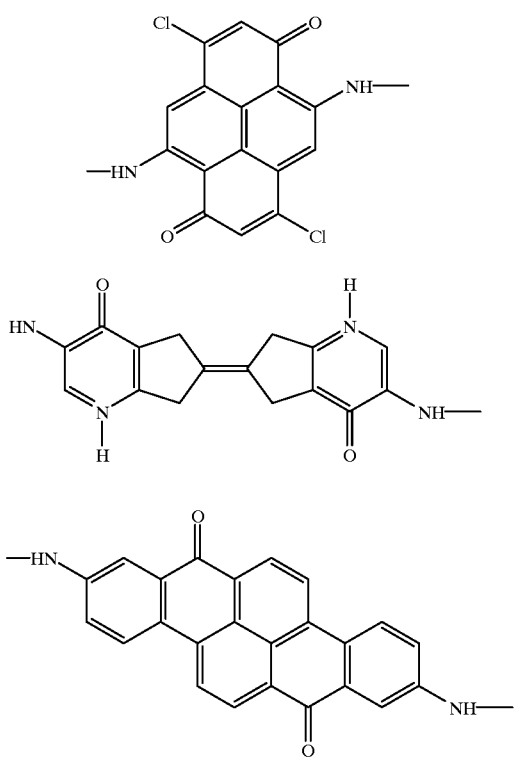
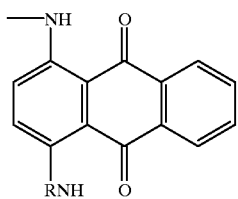
a
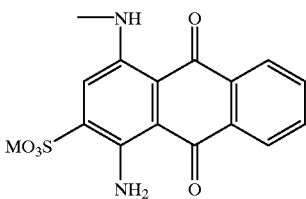
B
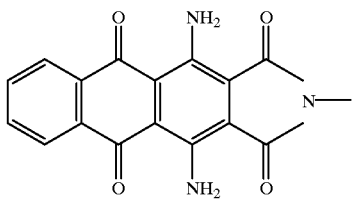
c
Formula XXXII:
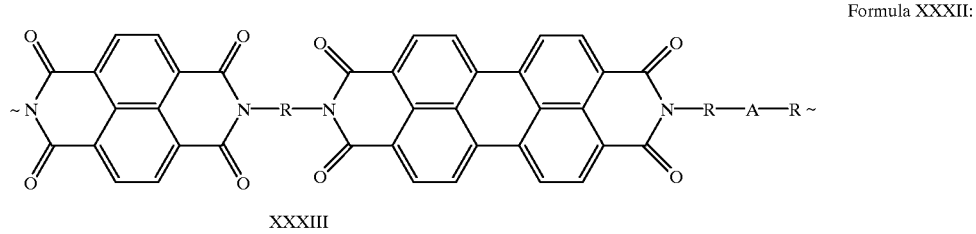
XXXIII
wherein R is as in formula XXII; and
A is as in formula XXXI.
Formula XXXIII:
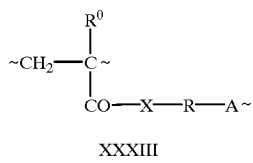
XXXIII
wherein M is a cation;
R is as in formula XXII and $(CH_2)n$ where n=3, 6;
$R^o$=H, $CH_3$;
X=NH, O; and
-continued
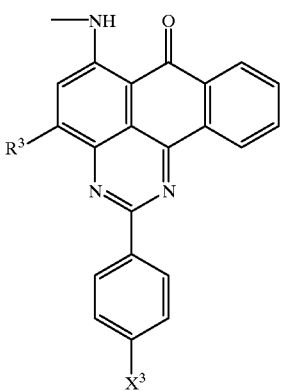
d -continued

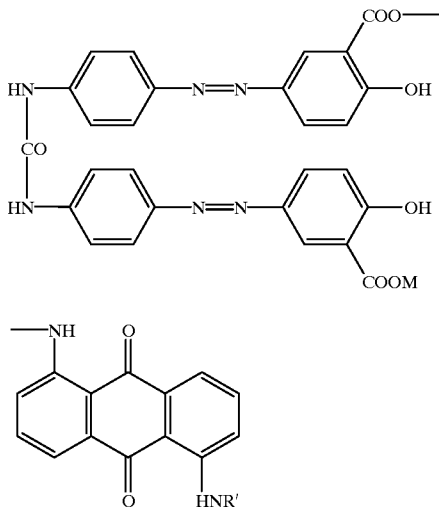

wherein the representations for A are: $R^3$=H, Br, $SO_3M$; and $X^3$=H, $SO_3M$.

Formula XXXIV:

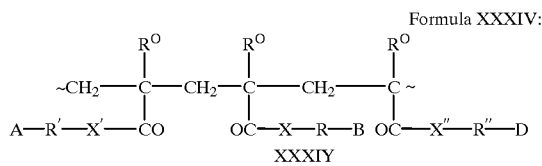

wherein M is a cation;
R, R', R" are the same as R in formula XXXIII;
$R^o$ is the same as in formula XXXIII;
X, X', X" are the same as X in formula XXXIII;
A, B, D are the same as A in formula XXXIII; and
$R^3$, $X^3$ are the same as in formula XXXIII.

In formulas I–XXXIV, "AR", "Ph", "Hal", "Alk", and "M" are as described below.

Ar is a substituted or unsubstituted phenyl radical. Suitable aryl groups are $C_6H_5$, Cl—$C_6H_4$, $C_6H_4SO_3M$. A suitable substituent for the phenyl radical is Cl.

Ph is a phenyl group.

Alk is an alkyl group, preferably with one to four carbon atoms.

Hal is a halide. Suitable halides include Cl, Br.

M is a cation. Preferred cations include $H^+$, $Li^+$, $Na^+$, $K^+$, $Cs^+$, or $NH_4^+$.

Modifying Additives

Modifying additives can be present in the liquid crystal material to enhance the polarizing efficiency (PE) of dichroic light polarizers based on the liquid crystal materials by reducing dispersion and reflectance of light at the interface of block microcrystalline structure which is formed during the formation of polarizing coating.

A modifying additive, when present in the liquid crystal material, is used to decrease the light dispersion in polarizing coatings which is due to the differences in the refractive index of dye, air, and substrate. In addition, a modifying additive can decrease the reflection and dispersion of light caused by the microdefects on the substrate surface.

A modifying additive is a low or high molecular organic compound of low volatility. The modifying additive can include various functional groups (such as, for example, OH, COOH, $CONH_2$, NH, CHO, CO, and the like. Exemplary suitable modifying additives include pentaerythritol, succinic aldehyde, hydroxycarboxylic acids, polyvinyl alcohol, polyalkylene glycols such as polyethylene glycol and polypropylene glycol, polyacrylic acid, polyacrylamide, polyethylene polyamines, polyethylenimine, and their copolymers, and the like.

Various lacquers, binders, and glue compositions including organoelemental compounds (e.g., organosilicon compositions) are also suitable modifying additives. In the liquid crystal material suitable lacquers, glues and binders mix with liquid crystal materials without destroying or disrupting the lyotropic liquid crystalline phase.

Polymers that are frequently used in liquid crystal materials such as poly-(p-benzamide), poly-(p-phenyleneterephthalimide), and cellulose esters (hydroxypropyl or ethyl derivatives) are also suitable.

The liquid crystal material contains, in addition to the dye and modifying additives, a solvent, and a surfactant. Surfactants are present in the formulation to provide better wetting of the substrate surface during the application of polarizing coatings. The nature of surfactant depends on the nature of substrate. Suitable surfactants include anionic detergents such as sodium dodecyl sulfate (SDS), deoxycholine, glycoholic acid, and cholic acid,; non-ionic surfactants such as NONIDET-P40, the glucopyranosides (n-dodecyl-glucopyranoside, n-heptyl-glucopyranoside, and polyoxyethylene ethers such as TRITON X-100, sodium perfluoroctanoate; polyvinyl alcohol; pentol; amidobetaine; and cationic surfactants such as dimethylbenzylalkyl ammonium chloride.

The liquid crystal material also contains a solvent. The nature of suitable solvents vary depending on the characteristics of the dye. For the dyes with polar groups such as —COOM, —$SO_3M$, —PO(OM)$_2$, the most suitable solvents are water and mixtures of water with alcohols, dioxane and lower ketones such as acetone, methylethylketone and the like.

For the most polymeric dyes (dyes of formulas XXII–XXXIV which do not contain groups such as —COOM and/or —$SO_3M$), the most suitable solvents are $H_2SO_4$ or oleum of various concentrations, and bipolar aprotic solvents such as dimethylformamide, dimethylsulfoxide (DMSO), N-methylpyrolyzone and the like. For the cationic dyes such as formulas XV–XVIII, and XX the most suitable solvents are water, acetic acid, diethylenglycol monoethyl ether or their mixtures.

In addition the liquid crystal material can include antioxidants and/or inhibitors. Antioxidants and inhibitors are conventionally introduced to ensure the chemical stability of polarizing coatings when used with lacquers, and glues, and do not differ from those used in the prior art. For purposes of the present invention, antioxidants and inhibitors can be used whether or not a glue or lacquer is present in the liquid crystal material. In addition, use of some glues and lacquers does not require presence of antioxidants and inhibitors in the liquid crystal material.

Modifying additives, when present in the compositions, provide a reduced level of the light scattering and reflection, thus increasing the polarization efficiency. The presence of modifying additives facilitates obtaining dichroic light polarizers with high polarization properties using organic dyes previously used in the liquid crystal materials that did not provide high polarization characteristics. In addition, the presence of modifying additives facilitates obtaining a more flat, uniform and mechanically stable coating, thus enhancing the quality and polarizing characteristics of dichroic light polarizers. In particular, use of a modifying additive produces a dichroic light polarizer having a $K_d$ above 15.

An important feature of the present invention is that the liquid crystal materials of the present invention contain dyes of formulas I–XXXIV, or their mixtures, that are capable of forming a liquid crystal phase. In molecules of dyes I–XXXIV, the vector of dipole moment of the optical transition (which determines the color of the polarizing coating) lies in the substrate plane or makes a small angle with this plane.

The use of dyes I–XXXIV in the liquid crystal material facilitates using a method of liquid crystal orientation based on the mechanical ordering. In this case, the ordering can be achieved through the development of shear stresses or by forces producing tensile deformation of the meniscus formed upon the disjoining tear-off of two surfaces with a liquid crystal layer between them. These techniques of liquid crystal orientation can be combined with application of the liquid crystal onto the substrate surface, e.g., by using a "roll-on-roll" technology. It is possible to use, as with prior art materials that did not provide high polarizing characteristics, various devices for the application of the coating, including flat slots, non-rotary (blade) and rotary (rolling cylinder) squeegees, and similar devices.

The use of modifying additives leads to the production of polarizing coatings with higher homogeneity and smoothness, thus significantly increasing the performance of dichroic light polarizers in comparison to the properties of devices based on currently used materials.

The liquid crystal material of this invention facilitates preparation of dichroic light polarizers on flat, spherical, and cylindrical solid surfaces. Suitable substrate materials include transparent and reflecting organic and inorganic glasses, silicate glass with a deposited semiconductor layer, silicon wafers with a deposited aluminum layer, etc. The polarizing coating can also be applied onto a flexible polymeric film, including films of poly(ethylene terephthalate), polycarbonate, triacetylcellulose, and other film materials.

The use of dyes of formulas I–XXXIV in the liquid crystal material also facilitates obtaining multilayer polymerizing by layer-by-layer deposition methods. In such cases, a polarizing film layer based on the same or a different dye can be applied immediately onto a previously formed layer or onto an intermediate film made of a transparent material. The polarization axis of the second layer can form an angle of 0 to 90° (degrees of arc) with respect to the polarization axis of the first layer.

Using sequential layer deposition technology, it is possible to obtain both colored and grey dichroic light polarizers with very high polarization characteristics. For example, a gray dichroic light polarizer can be obtained by sequential layers that are yellow, red, and blue. Similarly, a green dichroic light polarizer if formed of a yellow and a blue layer; violet of red and blue and so on.

The present invention facilitates preparation of dichroic light polarizers having a preset distribution of the orientation of polarization vectors and therefore, the color. The polarizing effect in a dichroic light polarizer of the present invention is created by a thin (generally 0.2–0.5$\mu$) layer of an organic dye oriented in a predetermined manner on the substrate surface. Such dichroic light polarizers can be made by the following method. The dye layer is obtained by applying a thin film of a solution of this dye, in the lyotropic liquid crystal state, to a substrate. The dye molecules are simultaneously oriented as the solution of dye is applied so that the liquid crystals in the resulting film have the desired distribution to be oriented in the base plane on the surface of the substrates to form the desired color. The molecules are oriented by viscoelastic forces that operate in a thin film of solution between the base plane and the film-applying device in the course of the base motion. Upon solvent removal, as by blowing the sample with warm air, the liquid crystals in the dye film retain the orientation of dye molecules produced as the liquid crystal material is applied.

The polarizing film can be imparted with additional properties by depositing (immediately or with an intermediate transparent layer), a second oriented layer of the same or a different dye. The direction of the polarization axis of the second layer may form an angle from 0 to 90° with the polarization axis of the first layer. When two sequential dye layers are formed using the same dye and have the same directions of polarization, the two-layer system can exhibit deeper color and higher polarization efficiency than a single layer system. If the second dye has an different color, the coincidence of the polarization directions in the two layers leads to a modification of the color of the polarizing coating.

For the mutually perpendicular polarization axes, rotation of the polarization plane of the light by 900 leads to a change ("switching") from one to another color of the system. For example, if an oriented layer of a blue dye is followed by a layer of red dye with a parallel orientation, the resulting polarizing coating has a nearly grey color. If the oriented layer of the blue dye is covered with a perpendicularly oriented layer of the red dye, the dichroic light polarizer switches color from blue to red. A multilayer structure using more than two dyes applied immediately one after another or with intermediate transparent layers can also be obtained.

To impart additional properties to the polarizing film after drying, the film can be also treated in a dye solution of a different color from the previous layer of the dye. Chemical bonding between the polarizing film and the molecules of dye applied to the film. This treatment either changes the color of the polarizing film or impart the property of color switching to the film as described more fully hereinafter. For example, if a thin molecular-ordered film of a dye of formula X, R=OCH$_3$, n=2 on a substrate surface is treated with an ethanol solution of yellow dye 2-[N'-methyl-N'-(4-methoxyphenyl)hydrozono]methyl-1,3,3'-trimethylindolynium chloride, which is a cationic dye, the latter is bound to the film in such a manner that the ground electronic transition in the molecules of this dye renders them predominantly oriented in the direction perpendicular to the moment of optical junction of the former dye.

The dye molecules in a solution can be bound to an ordered dye film without becoming oriented perpendicular to the dye film molecules. For example, this lack of orientation occurs when a film of a dye of formula X, R=OCH$_3$, n=2 is treated with an ethanol solution of red 4G dye (2-chloro-4-nitro-4'-[N-methyl-N-(2-trimethylammoniumethyl)amino]-azobenzene hydrosulfate). As a result, the ordered dye film changes the color in a polarized light from blue to violet.

The polarizing coatings obtained by this method can be formed on solid plates or polymer-based film substrates with the colored surface having a monochromatic or a polychromatic tint. The tint and the direction of macroscopic orientation of dye molecules (and, hence, that of the polarization vector) in the polarizing film can independently change in a preset manner in various regions of the plate surface, as described more fully hereinafter. Thus the polarizing coating can contain separate polarizing elements, with the direction of the polarization axis and/or the tint being unchanged within each element. This means that the direction of the polarization axis and/or the tint in each element remains independent of the direction of the polarization axis and/or the tint of other elements. In other words, the polarization axis and/or the tint are unchanged within the limits of one contour. The dimensions of such elements can vary from 100$\mu$ to 10 cm or more, depending on the technique employed for the film formation.

FIGS. 1$a$–1$h$ illustrate various types of dichroic light polarizers. For example, the dichroic light polarizer depicted in FIG. 1$a$ represents a monochromatic dichroic light polarizer having the direction of the polarization axis periodically changed by 90°. FIG. 1$b$ illustrates a monochromatic dichroic light polarizer having differing shapes of domains with various orientations of the polarization axis. FIGS. 1$c$ and 1$d$ illustrate variations of monochromatic patterns in which only a part of the surface (1$c$) or the entire surface except for a small region (1d) are occupied by a polarizing element. FIGS. 1e and 1f show colored variants, wherein regions with different tints $T_1$ and $T_2$ have parallel (1e) or perpendicular (1f) orientations of the polarization axes. The number of variants increases if when a two-layer polarizing coating system is used.

Figure 1B:
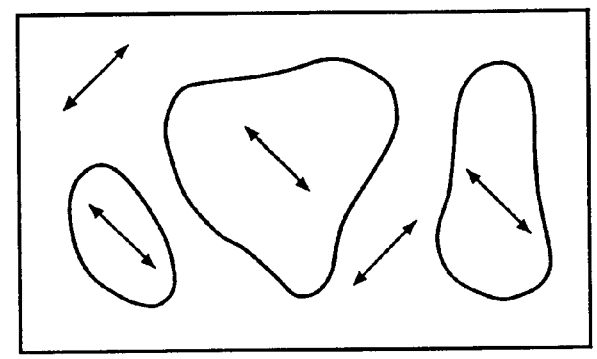
Figure 1A:
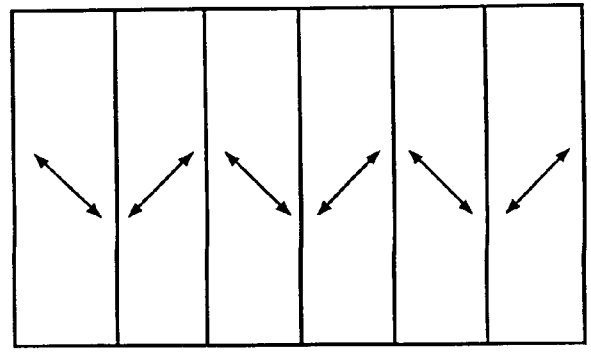
Figure 1H:
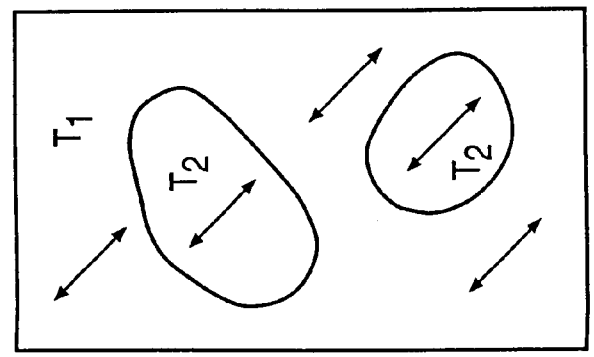
Figure 1G:
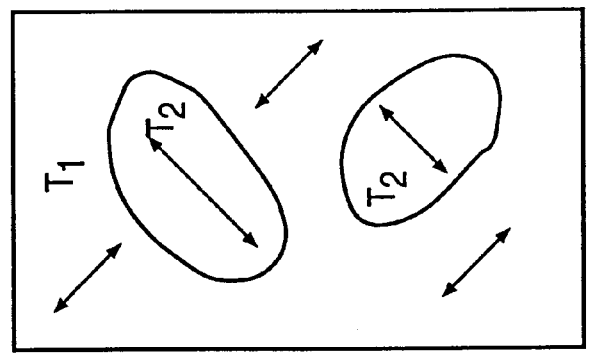
Figure 1F:
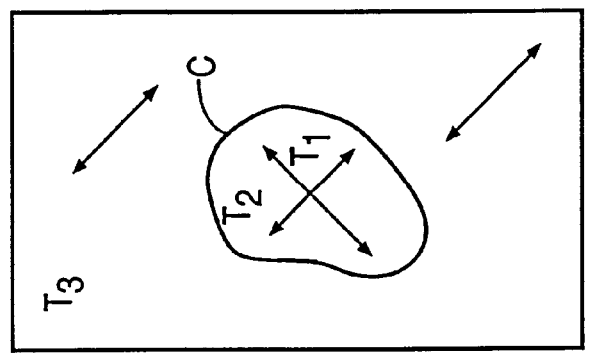
Figure 1E:
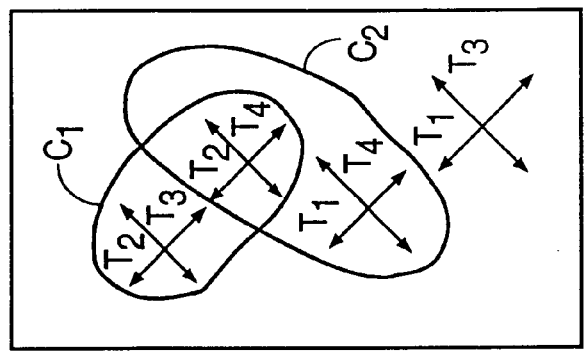

Alternate embodiments are illustrated in FIGS. 1g and 1h. In FIG. 1g, a bicolor domain with tinted regions $T_1$ and $T_2$, having mutually perpendicular orientations of the polarization axes, is surrounded with a domain of tint $T_3$, in which the polarization direction coincides with that of tint $T_2$. In FIG. 1h, the first oriented layer is colored by tint $T_1$, the domain bounded by contour $C_1$ has a tint $T_2$, the second layer is colored by tint $T_3$, and the domain bounded with contour $C_2$ has a tint $T_4$. In this embodiment, the directions of polarization of dyes $T_1$ and $T_2$ are parallel to one another and perpendicular to the direction of polarization of tints $T_3$ and $T_4$.

The dichroic light polarizers illustrated in FIGS. 1a–1h are used as follows. When illuminated by a nonpolarized light, the dichroic light polarizers illustrated in embodiments depicted in FIGS. 1a and 1b are uniformly colored over the entire area. Embodiments illustrated in FIGS. 1c and 1d exhibit regions of monochromatic color, while the embodiments in FIGS. 1e and 1f exhibit a film with alternating regions having different tints.

In polarized light, rotation of the dichroic light polarizer by 90° with respect to the light polarization plane in the embodiments in FIGS. 1a and 1b produce brightening of some regions and shadowing of other regions ("development" of a latent pattern). In the embodiment illustrated in FIGS. 1c and 1d, the monochromatic pattern observed in nonpolarized light is visible for one dichroic light polarizer orientation and invisible for another orientation. In the embodiment illustrated in FIG, 1e, the colored pattern will also appear for one DLP orientation and vanish for the other orientation. In the embodiment illustrated in FIG. 1f, one dichroic light polarizer orientation produces the disappearance of the regions of one tint, and upon a 90° rotation, the regions of the other tint disappear.

In the embodiment illustrated in FIG. 1g, the region of tint T, bounded with contour C, observed against a transparent background, changes the tint to $T_2$, and the background acquires tint $T_3$. In case 1h, one DLP orientation will show a region of tint $T_2$ bounded with contour C, observed against the background tint $T_1$, and the DLP rotation with change the pattern to region with tint $T_4$, bounded with contour $C_2$, against the background tint $T_3$. When the dichroic light polarizer devices depicted in FIGS. 1a–1f are additionally treated with a dye solution so that the DLP acquires the property of color switching, rotation of the dichroic light polarizer results in changing the tints of certain domains, rather than brightening of those regions.

Figure 2:
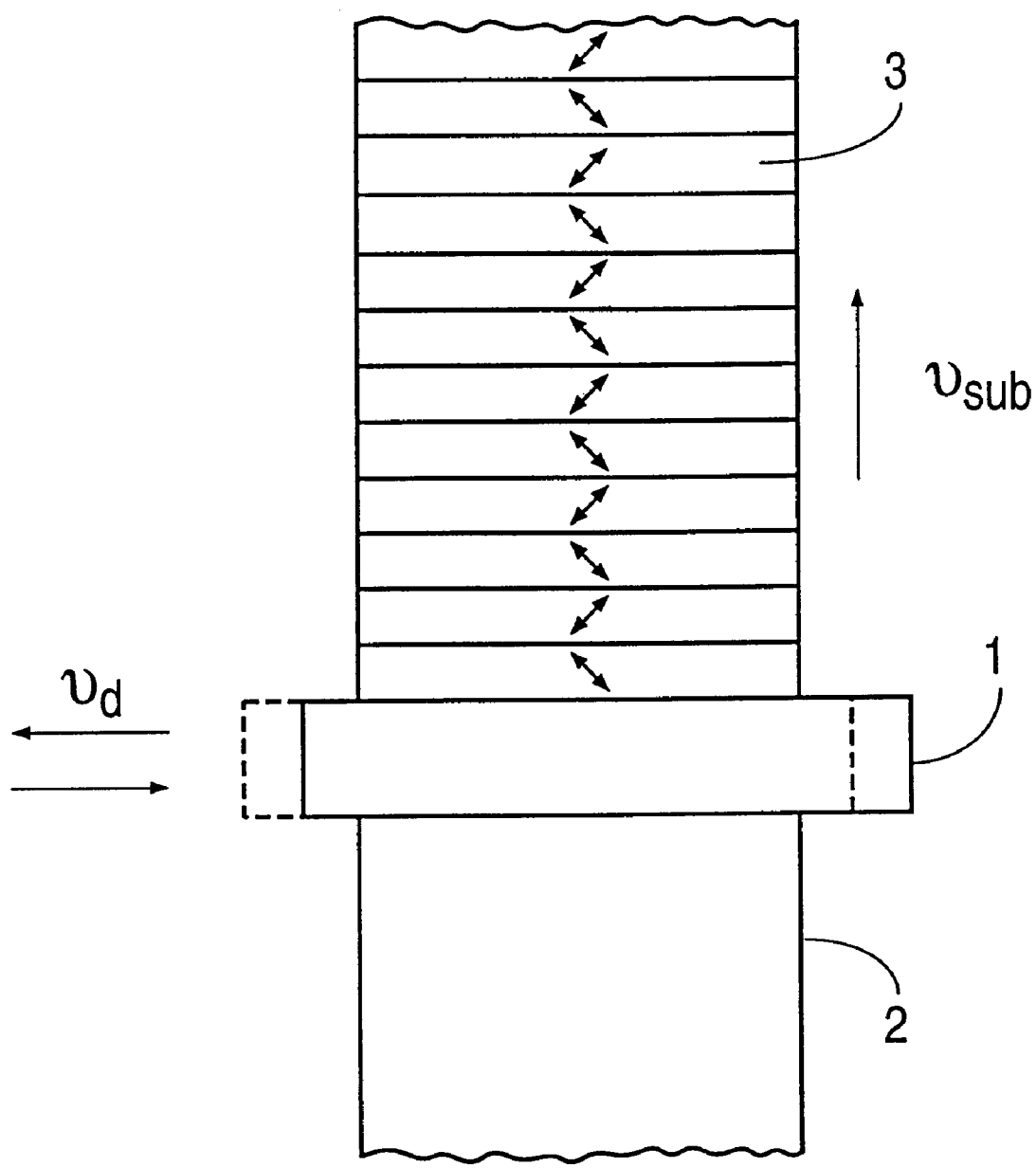
FIG. 2 illustrates a film-applying device preparing patterns of change of the polarization axis orientation with respect to the direction of substrate motion.
Figure 3D:
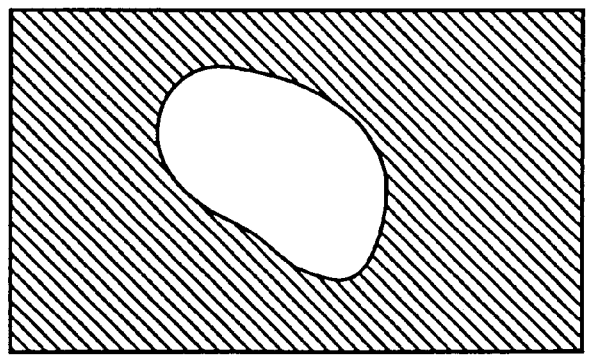
FIGS. 3(*a–d*) illustrate various engraving patterns on the surface of raster-profiled rollers, which produce dichroic light polarizers depicted in FIGS. 1(*a–d*)
Figure 3C:
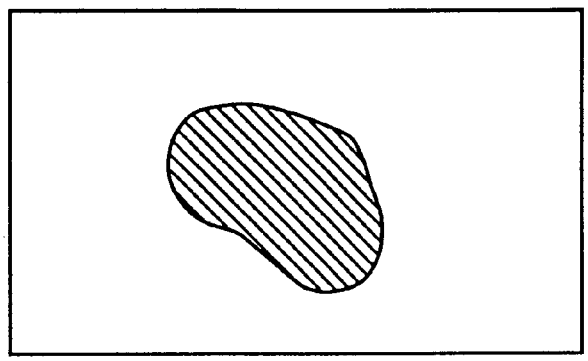
Figure 3B:
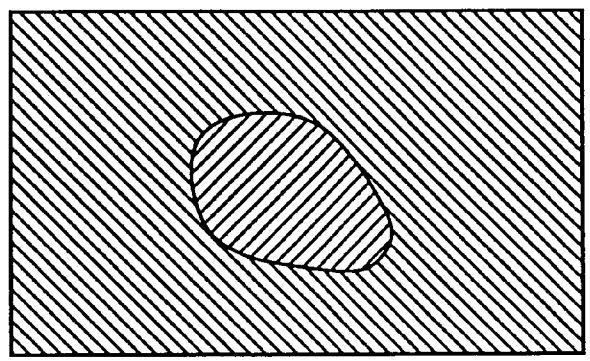
Figure 3A:
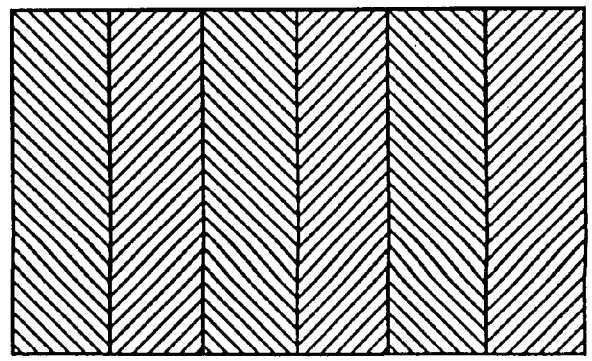

The layer of a liquid crystal material can be applied by conventional techniques such as by using a die, a squeegee, or a roller. For die or squeegee application techniques, a desired distribution of orientation of dye molecules is obtained by reciprocating motion of the die or squeegee (doctor plate) at a given velocity in a direction perpendicular to that of the substrate propagation. The velocity of the film-applying device and the time dependence of the motion velocity of the film-applying device determine the pattern of change of the polarization axis orientation with respect to the direction of substrate motion as illustrated in FIG. 2. For example, a uniform perpendicular motion of the device at a velocity equal to that of the substrate produces a polarization axis oriented at 45° relative to the direction of substrate motion that periodically changes its orientation by 90°. The half-period of this pattern equals to the amplitude of the reciprocating motion of the film-applying device. Generally, when the substrate and device are moved at velocities $V_{sub}$ (the velocity of the substrate) and $V_d$ (the velocity of the device), the orientation angle of the polarization vector ($\alpha$) with respect to the base motion direction is given by the formula:

$$\alpha = ctg(V_d/V_{sub})$$

wherein ctg is the cotangent. The substrate velocity can vary from 0.1 to 30 m/minute. The velocity of the film-applying device, can vary from 0 to 30 m/minute. The width of the half-period L during which the polarization has the same direction is determined by the formula:

$$L = aV_{sub}/V_d,$$

where a is the amplitude of the reciprocation motion of the film-applying device, which varies from 0 to 1 m.

To change the spatial orientation of the polarization axis when the film is applied using a rotating cylindrical roller, the property of liquid crystals flowing in a channel to acquire orientation parallel to the channel axis is used. The flow is created by a raster-profiled roller.

In particular, the surface of the roller contains grooves oriented at a given angle relative to the generating line, which determine the direction of the film polarization vector on the substrate surface. Alternatively, the grooves can be produced by wire wound on the roller at a given angle relative to the generating line, or by methods of mechanical of chemical engraving. The groove profile can be rectangular, triangular, trapezoidal, or rounded. The grooves is from about 50 to about 500$\mu$ wide, about 10 to about 100$\mu$ deep. The wall width at top is about 10 to about 50$\mu$.

Using a raster-profiled roller with an appropriate pattern of groove orientations, polarization patterns of various shapes, with differing orientations of the polarization axis in various regions can be formed. By sequentially employing several rollers and dyes with various colors, colored patterns can also be prepared.

Figure 4:
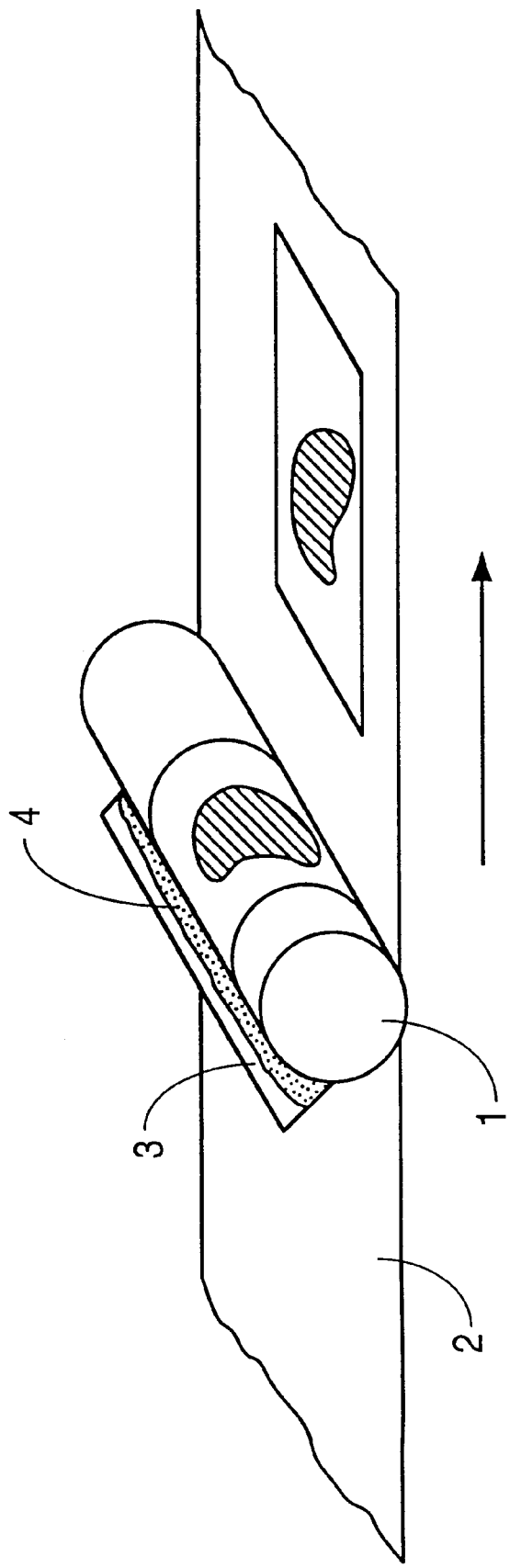
FIG. 4 illustrates the process of polarization pattern formation with the aid of a profiled roller.

FIGS. 3a–3d illustrate various engraving patterns on the surface of raster-profiled rollers, which produce polarizing coatings depicted in FIGS. 1a–1d. FIG. 4 illustrates the process of polarization pattern formation with the aid of such a profiled roller. In the Figure, roller 1 is pressed against a polymeric base 2 and rolled by its surface without slippage. Squeegee 3 removes excess dye 4. The dye remaining in the grooves is transferred by roller onto the substrate surface 2 so that the direction of the polarization axis of the coating coincides with the orientation of grooves. By sequentially using several (e.g., two) rollers and dyes of various tints, polychromatic coatings, such as the patterns depicted in FIGS. 1e and 1f and the multilayer polarizing coatings such as the embodiments illustrated in FIGS. 1g and 1h can be produced.

Figure 5:
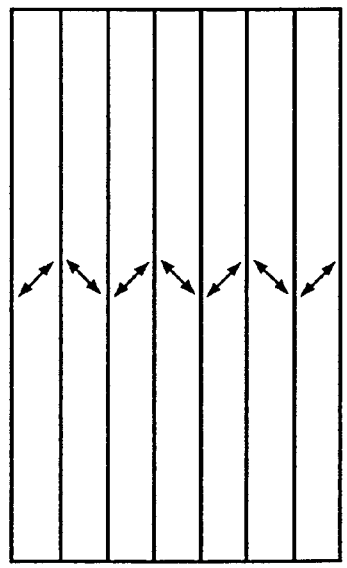
FIG. 5 illustrates formation of periodicity in a polarizing coating that is perpendicular to the direction of the base motion of the roller.
Figure 6:
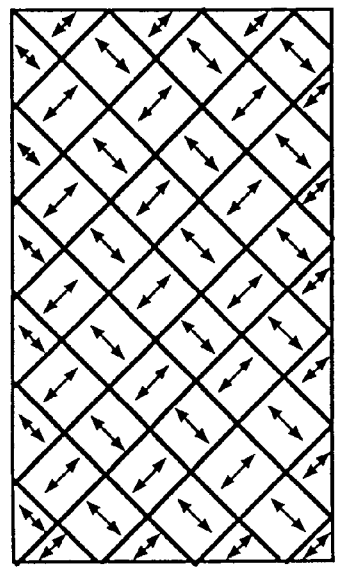
FIG. 6 illustrates neighboring cells of a polarizing coating in which the polarization axes are mutually perpendicular.

In particular, this method can produce polarizing coatings with periodically changed orientation of the is polarization axis. For example, by forming a pattern of zig-zag grooves with a 90° angle between the straight segments and the zig-zag direction perpendicular to the generating line of the roller, a polarizing coating with a periodic change in the polarization vector orientation in the direction of base motion can be obtained as illustrated in FIG. 1a. When the zig-zag line is directed along the generating line of the roller, the periodicity is formed in the direction perpendicular to that of the base motion as illustrated in FIG. 5. If the grooves form square cells with mutually perpendicular directions to that of the neighboring cells, the resulting polarizing coating has a checkerboard pattern of the polarization axis orientations. The polarization axes in the neighboring cells can also be mutually perpendicular as illustrated in FIG. 6.

Application of the liquid crystal material of the present invention proposed allows various glues to be employed for the production of laminated structures such as triplex glasses and multilayer films. Such laminated structures can be used in the automotive industry for windshields and in architectural applications where severe conditions require resistance to heat, impact, and other stresses.

The above properties indicate that the liquid crystal materials can be used in the production of dichroic light polarizers for a variety of applications. High polarization efficiency of the polarization coatings allow the dichroic light polarizers to be employed in liquid crystal displays and indicators.

This invention is further illustrated by the following specific but non-limiting examples. Temperatures are given in degrees Centigrade and concentrations as weight percent unless otherwise specified. Procedures which are constructively reduced to practice are described in the present tense, and procedures which have been carried out in the laboratory are set forth in the past tense. In the examples, the elemental analysis for each sample was determined twice. All citations in the above specification and the following examples are incorporated herein by reference in their entireties.

EXAMPLE 1

Preparation of a Polarizing Coating

Using a Dye of Formula I

In this example, a dye of formula I was synthesized and used to prepare polarizing coatings by various procedures.
Synthesis of Dye In this example, a dye of formula I in which R=H, M=H$^+$, n=2, was prepared by the following sulfonation procedure.

A vat yellow 4 (59100 C.I.) dye (5 g) is dissolved in 45–50% oleum (50 ml) to form a reaction mixture. The reaction mixture is heated to 80° C. and maintained at this temperature for 7 hours. The reaction mixture is then diluted with 170 ml water, and 40 g sodium chloride is added. The reaction mixture suspension is heated to 80° C., maintained at this temperature for 10 minutes, and filtered in the hot state. The residue is pressed and washed with a 13% solution of sodium chloride until no sulfate anions are detected in the filtrate. The residue is dried, boiled in 30 ml of 16% hydrochloric acid, and filtered to form a final residue. The final residue is washed with 10% hydrochloric acid, then with isopropyl alcohol, and dried.

This sulfonation procedure yielded 5.06 g dye with formula I, n=2. The elemental analysis calculated for $C_{24}H_{12}O_8S_2 \cdot 4H_2O$ was S 11.37. The elemental analysis determined was S 11.69, 11.88.

The above sulfonation procedure was repeated using anthanthrone (5.0 g) instead of vat yellow 4 dye and produced 4.85 g dye of formula IV, n=2. The elemental analysis calculated for $C_{23}H_{11}O_8S_2$ was S 13.37. The elemental analysis determined was S 13.12, 13.56.

The above sulfonation procedure was repeated using isoviolanthrone (5 g) instead of vat yellow 4 dye and produced 5.38 g dye of formula IX, n=3. The elemental analysis calculated for $C_{34}H_{16}O_{11}S_3 \cdot 3H_2O$ was S 12.82. The elemental analysis determined was S 12.58, 13.23.

The above sulfonation procedure was repeated using violanthrone (5 g) instead of vat yellow 4 dye and produced 5.5 g dye of formula X, n=4. The elemental analysis calculated for $C_{34}H_{16}O_{14}S_4 \cdot 4(H_2O)$ was S 15.09. The elemental analysis determined was S 14.80, 14.95.

The above sulfonation procedure was repeated using a grey C vat dye (5 g) instead of vat yellow 4 dye and produced 6.7 g dye of formula XIII, n=4. The elemental analysis calculated for $C_{45}H_{21}N_3O_{16}S_4 \cdot 4(H_2O)$ was S 12.09. The elemental analysis determined was S 11.78, 11.80.

Preparation of a Lyotropic Liquid Crystal Dye Phase

A lyotropic liquid crystal dye phase using a dye of formula I was prepared as described in the three methods below.

Method 1

2.5 g of dye prepared as describe above free of mineral impurities is dissolved by heating in 7.5 ml of distilled water to form a reaction mixture. The reaction mixture is cooled to room temperature, and the pH of the reaction mixture is adjusted to pH 5–6, using a base solution (e.g., 2 moles of ammonia or an alkali metal hydroxide and 1 mole of dye). The presence of a liquid crystal phase in the reaction mixture is monitored by using a polarization microscope equipped with two crossed polarizers.

0.25 g surfactant (Triton X-100), 0.05 g hydroquinone, and 1.0 g polyethylene glycol is added with mixing to the liquid crystal phase-containing reaction mixture to form a liquid crystal material. The liquid crystal material is used to produce a polarization coating on a substrate surface, as described below.

Method 2

2.5 g of dye of formula I, n=2, free of mineral impurities, is dissolved by heating in a mixture of 75 ml water and 25 ml isopropyl alcohol to form a reaction mixture. 10% ammonia solution is added to the reaction mixture until reaching a pH of 5–6. The reaction mixture is filtered from mechanical impurities and concentrated to a total mass of 10 g by evaporating the solvent. Yield, 10 g of a liquid crystal phase.

Method 3

Liquid crystals based on the polymeric dyes with formulas XXII–XXXIV were prepared using the following solvents: sulfuric acid of various concentrations, dimethylformamide, dimethylsulfoxide, dimethylacetamide, and N-methylpyrrolidone. All the fabrication methods below were performed using the following formulation of the liquid crystal material:

| | |
|---|---|
| Dye formula I, R = H, n = 2 | 21.00% |
| TRITON X-100 | 2.10% |
| Hydroquinone | 0.42% |
| Polyethylene glycol | 8.40% |
| Water | 68.08% |

Fabrication of Dichroic Light Polarizers

Application of Polarization Coatings onto Poly(ethylene terephthalate) Films

Coating Application with a Flat Die: All applications of polarizing films described below were performed at a temperature of 20–25° C. and a relative humidity of 70%.

A flat die was coated as described below.

A polyethylene terephthalate (PET) film with a thickness of 50$\mu$, a width 120 mm, and a length 1000 mm is placed between the pressing cylinder (diameter 40 mm, length 200 mm) and a die. The die had a volume of 5 ml and a slit with a width of 300$\mu$ and a length of 100 mm. The working surfaces of the die, particularly the edge, are thoroughly polished. The PET film is pressed against the die surface with a strength of about 10 Newtons (N).

The liquid crystal is poured into the die. The film is moved at a rate of 150 mm/second to form an oriented dye layer on the film surface. After drying, the surface film has a transmission of To=40% and a $K_d$ value of 15.6 at maximum absorption.

Coating Application with a Non-rotary Cylindrical Squeegee: PET film is passed between two steel cylinders (diameter 20 mm, length 1000 mm) with thoroughly polished surfaces. The thickness of the polarizing coating is determined by 60$\mu$ thick spacers situated at the cylinder ends. An aliquot of a liquid crystal phase (2 ml) is applied onto the film surface to form a 5–10 mm wide band immediately before the cylinder. Then the film is moved between cylinders at a velocity of 150 mm/second. After drying, the polarizing coating had the following properties: To=38%, $K_d$=15.

Coating Application with a Rolling Cylinder: A cylinder with a diameter of 20 mm and a length of 200 mm is mounted over a flat surface. The cylinder cannot move along the surface, but can rotate about its axis. The ends of the cylinder carry spacer rings with a thickness of $10\mu$. One end of a substrate film is passed under the cylinder and the flat base. An aliquot (about 1 ml) of a liquid crystal is placed in the form of a band before the cylinder and the film is moved at a velocity of 50 mm/s. After drying, the polarizing coating has the following properties: To=45%, K=17.

Coating Application by Disjoining Tear-off of Two Films: Two immobile cylinders (diameter 20 mm, length 200 mm) spaced by $110\mu$ are mounted at a height of 150 mm over a table. The ends of two polymeric films with thicknesses $50\mu$ are passed between cylinders by a distance of 150 mm. A 0.5 ml volume of a liquid crystal is introduced between cylinders on the surface of both films. Then the films are drawn downward at a velocity of 50 mm/second and simultaneously moved apart. After drying, the polarizing coating has the following properties: To=45%, K=16.8.

Deposition of Polarization Coatings onto a Solid Substrate

Coating Application with a Non-rotary Cylindrical Squeegee: A glass plate (100×100 mm$^2$, thickness 2 mm) is thoroughly washed and dried. A 1 ml volume of a liquid crystal dye is applied to form a band along the plate edge. The plate is fixed on a table that can perform translational motion. A non-rotary cylindrical squeegee (diameter 20 mm, length 200 mm) is pressed against the plate. The thickness of the dye layer is controlled by two spacers with a thickness of $10\mu$ and a width of 5 mm, fixed at a distance of 80 mm on the cylinder surface. The table with the plate is moved at velocity of 100 mm/second with respect to the immobile cylinder. After drying, the polarizing coating has the following properties: To=43%, $K_d$=16.0.

Coating Application with a Rolling Cylinder: A glass plate with an aliquot of a liquid crystal dye is fixed on a movable table as described in section. Two spacers with a thickness $10\mu$ and a width of 5 mm are fixed at the longitudinal edges of the plate. A cylinder (diameter 20 mm, length 200 mm), capable of rotating about its own axis, is placed at the end of the table. The table is moved at a velocity of 20 mm/second relative to the cylinder, so that the cylinder rolls on the plate surface. As a result, the liquid crystal dye is uniformly spread and oriented on the plate surface. After drying the polarizing coating has the following properties: To=45%, $K_d$=15.0.

Coating Application by Tear-off of a Polymeric film from a Solid Surface: A glass plate is prepared as described immediately above and has two spacers (thickness $10\mu$) positioned at the longitudinal edges of the plate. A 0.3 ml volume of a liquid crystal is applied at the transverse plate edge. The plate is covered with a PET film (width 80 mm, length 100 mm, thickness $2\mu$), and the liquid crystal material is spread over the plate surface by using a roll. Finally, the polymeric film is torn-off from the plate, beginning at one of the transverse edges, at a velocity of 50 mm/second. After drying, the polarizing coating has the following properties: To=44%, $K_d$=16.2.

EXAMPLE 2

Synthesis of a Dye of Formula I

Synthesis of a dye of formula I, R=H, M=H$^+$, n=3 was performed as described below.

A vat yellow 4 (59100 C.I.) dye (5 g) is dissolved in 45–50% oleum (50 ml). Then mercury sulfate (0.03 g) is added to form a reaction mixture. The reaction mixture is heated to 1150C. After keeping the mixture at 110–120° C. for 8 hours, the reaction mixture is diluted with water to a sulfuric acid concentration of 50%, and 25 g sodium chloride is added. The reaction mixture suspension is heated to 80° C. and filtered in the hot state. The residue is washed with a 12 solution of sodium chloride, 16% hydrochloric acid, and isopropyl alcohol, and dried to yield 5.4 g dye with formula I, n=3. The elemental analysis calculated for $C_{24}H_{12}O_{11}S_3.3(H_2O)$ was S 15.36. The elemental analysis determined was S 14.89, 15.03.

The sulfonation procedure described in this example was repeated using vat orange 1 (59105 C.I.) dye (5 g) instead of vat yellow 4 dye and produced a dye of formula I, R=Br, n=2. The elemental analysis calculated for $C_{24}H_{10}Br_2O_8S_2.2(H_2O)$ was Br 23.32; S 9.33. The elemental analysis determined was Br 23.44, 23.68; S 9.00, 9.12.

The sulfonation procedure described in this example was repeated using 3,9-di(anthraquinonyl-1-amino) dibenzepyrenquinone (5.0 g) instead of vat yellow 4 dye and produced 6.2 g dye of formula I, and produced a dye of formula I, R=anthraquinonyl-1-amino, n=4. The elemental analysis calculated for $C_{52}H_{28}N_2O_{18}S_4.4(H_2O)$ was N 2.39; S 10.96. The elemental analysis determined was N 2.40, 2.54; S 10.78, 10.81.

The sulfonation procedure described in this example was repeated using a vat orange 11 (70805 C.I.) dye (5 g) instead of vat yellow 4 dye and produced 5.6 g dye of formula II, n=4. The elemental analysis calculated for $C_{42}H_{18}N_2O_{18}S_4$ was S 13.25; N 2.90. The elemental analysis determined was S 12.97, 12.68; N 2.56, 2.64.

The sulfonation procedure described in this example was repeated using vat grey '2S' dye (5 g) instead of vat yellow 4 dye and produced 6.0 g dye of formula IV, R=anthraquinonyl-1-amino, n=4. The elemental analysis calculated for $C_{50}H_{24}N_2O_{18}S_4.4(H_2O)$ was N 2.46; S 11.23. The elemental analysis determined was N 2.36, 2.61; S 10.98, 11.00.

The sulfonation procedure described in this example was repeated using a vat green 3 (69599 C.I.) dye (5 g) instead of vat yellow 4 dye and produced 5.2 g dye of formula XII, R=H, n=3. The elemental analysis calculated for $C_{31}H_{15}NO_{12}S_3.3(H_2O)$ was S 12.94; N 1.88. The elemental analysis determined was S 12.24, 12.57; N 1.80, 2.01.

The sulfonation procedure described in this example was repeated using the 9-bromo derivative of vat green 3 (69500 C.I.) dye (5 g) instead of vat yellow 4 dye and produced 4.8 g dye of formula XII, R=Br, n=2. The elemental analysis calculated for $C_{31}H_{14}BrNO_9S_2.4(H_2O)$ was S 8.44; Br 9.73; N 1.70. The elemental analysis determined was S 7.98, 8.12; Br, 9.55, 9.60; N 1.45, 1.67.

The sulfonation procedure described in this example was repeated using a vat black 25 (69525 C.I.) dye (5 g) instead of vat yellow 4 dye and produced 6.1 g dye of formula XII, R=anthraquinonyl-1-amino, n=4. The elemental analysis calculated for $C_{45}H_{22}N_2O_{17}S_4.4(H_2O)$ was S 12.08. The elemental analysis determined was S 11.57, 11.88.

EXAMPLE 3

Synthesis of a Dye of Formula III

A dye of formula III, R=H, n=2 was prepared as described below.

5 g diphthaloylcarbazole is dissolved in a mixture of 20% oleum (10 ml) and chlorosulfonic acid (20 ml) to form a reaction mixture. The reaction mixture is heated at 85–90° C. for 10–12 hours. The reaction mixture is then cooled and diluted with water to a sulfuric acid concentration of 50%. The residue in the reaction mixture is filtered, washed with 16% hydrochloric acid, and dried. The product is dissolved in 150 ml water at pH 6, and 100 ml isopropyl alcohol is added. The precipitate is filtered, washed with a water-isopropanol mixture (1:1 v/v), and dried to yield 5.8 g dye with formula III, R=H, n=2. The elemental analysis calculated for $C_{28}H_{13}NO_{10}S_2.4(H_2O)$ was S 9.73; N 2.12. The elemental analysis determined was S 9.34, 9.65; N 2.00, 2.35.

The sulfonation procedure described in this example was repeated using 4,5'-dibenzoylaminodiphthaloylcarbazole dye (5 g) instead of diphthaloylcarbazole dye and produced 5.1 g dye of formula III, R=NHCOPh, n=3. The elemental analysis calculated for $C_{42}H_{23}N_3O_{15}S_3.3(H_2O)$ was S 10.94; N 4.38. The elemental analysis determined was S 10.36, 10.55; N 4.07, 4.26.

The sulfonation procedure described in this example was repeated using 5,5'-dibenzoylaminodiphthaloylcarbazole dye (5 g) instead of diphthaloylcarbazole and produced 5.0 g dye of formula III, R=NHCOPh, n=4. The elemental analysis calculated for $C_{42}H_{23}N_3O_{18}S_3$ was S 12.13; N 4.26. The elemental analysis determined was S 11.87, 11.98; N 3.98, 4.11.

The sulfonation procedure described in this example was repeated using 1,4,5,8-naphthalinetetracarboxylic acid (NTCA) hydroxyphenylimide methylbenzimidazole dye (5 g) instead of diphthaloylcarbazole dye and produced 5.3 g dye of formula V, R=OH, R'=CH$_3$, n=3. The elemental analysis calculated for $C_{27}H_{15}N_3O_{13}S_3.3(H_2O)$ was N 5.68; S 12.99. The elemental analysis determined was N 5.33, 5.60; S 12.00, 12.23.

The sulfonation procedure described in this example was repeated using NTCA butylphenylimide chlorobenzimidazole dye (5 g) instead of diphthaloylcarbazole dye and produced 4.8 g dye of formula V, R=C$_4$H$_9$, R'=Cl, n=2. The elemental analysis calculated for $C_{30}H_{20}ClN_3O_9S_2.2(H_2O)$ was Cl, 5.06; N 5.99; S 9.12. The elemental analysis determined was Cl, 4.68, 5.12; N 5.33, 5.60; S 8.90, 9.23.

The sulfonation procedure described in this example was repeated using NTCA ethoxyphenylimide methylbenzimidazole dye (5 g) instead of diphthaloylcarbazole dye and produced 5.4 g dye of formula V, R=C$_2$H$_5$O, R'=CH$_3$, n=3. The elemental analysis calculated for $C_{29}H_{19}N_3O_{13}S_3.3(H_2O)$ was N 5.48; S 2.52. The elemental analysis determined was N 5.00, 5.32; S 11.90, 12.45.

The sulfonation procedure described in this example was repeated using NTCA bromophenylimide methylbenzimidazole dye (5 g) instead of diphthaloylcarbazole dye and produced 5.0 g dye of formula V, R=Br, R'=CH$_3$, n=2. The elemental analysis calculated for $C_{29}H_{19}N_3O_{13}S_3.3(H_2O)$ was N 5.48; S 12.52. The elemental analysis determined was Br, 10.77, 10.98; N 5.45, 5.71; S 9.56, 9.79.

The sulfonation procedure described in this example was repeated using 3,4,9,10-perylenetetracarboxylic acid (PTCA) hydroxyphenylimide methylbenzimidazole dye (5 g) instead of diphthaloylcarbazole dye and produced 5.5 g dye of formula VI, R=OH, R'=CH$_3$, n=3. The elemental analysis calculated for $C_{31}H_{19}N_3O_{13}S_3.3(H_2O)$ was N 5.32; S 12.14. The elemental analysis determined was N 5.54, 5.76; S 11.87, 12.00.

The sulfonation procedure described in this example was repeated using PTCA butylphenylimide chlorobenzimidazole dye (5 g) instead of diphthaloylcarbazole dye and produced 5.2 g dye of formula VI, R=C$_4$H$_9$, R'=Cl, n=2. The elemental analysis calculated for $C_{34}H_{24}ClN_3O_9S_2.2(H_2O)$ was Cl 4.71; N 5.57; S 8.49. The elemental analysis determined was Cl, 4.32, 4.40; N 5.34, 5.39; S 8.90, 9.34.

The sulfonation procedure described in this example was repeated using 3,4,9,10-anthanthronetetracarboxylic acid (AATCA) methoxyphenylimide benzimidazole dye (5 g) instead of diphthaloylcarbazole dye and produced 5.7 g dye of formula VII, R=CH$_3$O, R=H, n=3. The elemental analysis calculated for $C_{39}H_{17}N_3O_{15}S_3.3(H_2O)$ was N 4.75; S 10.85. The elemental analysis determined was N 4.59, 4.76; S 10.45, 10.51.

The sulfonation procedure described in this example was repeated using AATCA methylphenylimide bromobenzimidazole dye (5 g) instead of diphthaloylcarbazole dye and produced 4.5 g dye of formula VII, R=CH$_3$, R'=Br, n=2. The elemental analysis calculated for $C_{39}H_{16}BrN_3O_{11}S_2.2(H_2O)$ was Br 9.07; N 4.76; S 7.26. The elemental analysis determined was Br 8.56, 8.70; N 4.33, 4.50; S 7.69, 7.90.

The sulfonation procedure described in this example was repeated using dihydroxyisoviolanthrone dye (5 g) instead of diphthaloylcarbazole dye and produced 5.1 g dye of formula IX, R=OH, n=2. The elemental analysis calculated for $C_{34}H_{16}O_{10}S_2.2(H_2O)$ was S 9.37. The elemental analysis determined was S 8.98, 9.08.

The sulfonation procedure described in this example was repeated using dimethoxyisoviolanthrone dye (5 g) instead of diphthaloylcarbazole dye and produced 5.0 g dye of formula IX, R=CH$_3$, n=2. The elemental analysis calculated for $C_{36}H_{18}O_{10}S_2.2(H_2O)$ was S 9.03. The elemental analysis determined was S 9.65, 9.49.

The sulfonation procedure described in this example was repeated using dimethoxyviolanthrone dye (5 g) instead of diphthaloylcarbazole dye and produced 4.9 g dye of formula X, R=CH$_3$, n=2. The elemental analysis calculated for $C_{36}H_{18}O_{10}S_2.2H_2O$ was S 9.03. The elemental analysis determined was S 9.75, 9.60.

The sulfonation procedure described in this example was repeated using dianilinodichloropyrenequinone dye (5 g) instead of diphthaloylcarbazole dye and produced 5.2 g dye of formula XI, R=H, n=2. The elemental analysis calculated for $C_{28}H_{18}Cl_2N_2O_8S_2.2(H_2O)$ was S 9.42. The elemental analysis determined was S 9.88, 9.95.

The sulfonation procedure described in this example was repeated using di(4-chloroanilino)dichloropyrenequinone dye (5 g) instead of diphthaloylcarbazole dye and produced 4.8 g dye of formula XI, R=4-Cl, n=2. The elemental analysis calculated for $C_{28}H_{16}Cl_4N_2O_8S_2.2(H_2O)$ was S 8.55. The elemental analysis determined was S 8.78, 8.90.

The sulfonation procedure described in this example was repeated using a vat grey 'S' dye (5 g) instead of diphthaloylcarbazole dye and produced 5.2 g dye of formula XIII, n=3. The elemental analysis calculated for $C_{45}H_{21}N_3O_{13}S_3$ was S 10.60. The elemental analysis determined was S 10.97, 11.21.

EXAMPLE 4

Synthesis of a dye with formula V, wherein R=R'=H, M=H$^+$, n=2, was performed by the sulfonation procedure described below.

NTCA phenylimide benzimidazole (10 g) is dissolved in 10% oleum (50 ml) to form a reaction mixture. The reaction mixture is heated at 80–85° C. for 4 hours. Then, the reaction mixture is cooled and diluted with 100 ml water. The resultant precipitate is filtered, washed with concentrated hydrochloric acid until no sulfate anions are detected in the filtrate, and dried to yield 12.45 g of a dye with formula V, R=R'=H, n=2. The elemental analysis calculated for $C_{26}H_{13}N_3O_9S_2.2(H_2O)$ was N 7.30; S 11.13. The elemental analysis determined was N 6.98, 7.10; S 11.67, 11.73.

The sulfonation procedure described in this example was repeated using NTCA methoxyphenylimide benzimidazole dye (10 g) instead of NTCA phenylimide benzimidazole dye and produced 13.2 g dye of formula V, R=CH$_3$O, R'=H, n=2. The elemental analysis calculated for $C_{27}H_{15}N_3O_{10}S_2.2$ ($H_2O$) was N 6.55; S 9.98. The elemental analysis determined was N 6.33, 6.40; S 10.34, 10.50.

The sulfonation procedure described in this example was repeated using NTCA 4-phenylaminophenylimide benzimidazole dye (10 g) instead of NTCA phenylimide benzimidazole dye and produced 15.0 g dye of formula V, R=NHPh, R'=H, n=4. The elemental analysis calculated for $C_{32}H_{18}N_4O_{15}S_4 \cdot 4(H_2O)$ was N 6.24; S 14.25. The elemental analysis determined was N 5.89, 6.10; S 13.90, 14.11.

The sulfonation procedure described in this example was repeated using NTCA 4-phenyloxyphenylimide benzimidazole dye (10 g) instead of NTCA phenylimide benzimidazole dye and produced 12.3 g dye of formula V, R=$OC_6H_5$, R'=CH3, n=3. The elemental analysis calculated for $C_{33}H_{19}N_3O_{13}S_3 \cdot 3(H_2O)$ was N 5.15; S 11.78. The elemental analysis determined was N 4.78, 5.10; S 11.45, 11.63.

The sulfonation procedure described in this example was repeated using PTCA phenylimide benzimidazole dye (10 g) instead of NTCA phenylimide benzimidazole dye and produced 11.8 g dye of formula VI, R=R'=H, n=2. The elemental analysis calculated for $C_{30}H_{17}N_3O_9S_2 \cdot 2(H_2O)$ was N 6.33; S 9.65. The elemental analysis calculated for N 5.87, 5.90; S 9.99, 10.12.

The sulfonation procedure described in this example was repeated using PTCA methoxyphenylimide benzimidazole dye (10 g) instead of NTCA phenylimide benzimidazole dye and produced 12.0 g dye of formula VI, R=$CH_3O$, R'=H, n=2. The elemental analysis calculated for $C_{31}H_{19}N_3O_{10}S_2 \cdot 2(H_2O)$ was N 5.91; S 9.00. The elemental analysis determined was N 5.34, 5.60; S 9.45, 9.63.

The sulfonation procedure described in this example was repeated using PTCA 4-phenylaminophenylimide benzimidazole dye (10 g) instead of NTCA phenylimide benzimidazole dye and produced 14.5 g dye of formula VI, R=NHPh, R=NHPh, R'=H, n=4. The elemental analysis calculated for $C_{36}H_{22}N_4O_{15}S_4 \cdot 4(H_2O)$ was N 5.89; S 13.47. The elemental analysis determined was N 5.46, 5.66; S 13.00, 13.47.

The sulfonation procedure described in this example was repeated using PTCA ethoxyphenylimide bromobenzimidazole dye (10 g) instead of NTCA phenylimide benzimidazole dye and produced 10.5 g dye of formula VI, R=$C_2H_5O$, R'=Br, n=2. The elemental analysis calculated for $C_{32}H_{20}BrN_3O_{10}S_2 \cdot 2(H_2O)$ was Br, 10.18; N 5.34; S 8.14. The elemental analysis determined was Br, 9.78, 9.90; N 4.98, 5.12; S 8.23, 8.45.

The sulfonation procedure described in this example was repeated using AATCA phenylimide benzimidazole dye (10 g) instead of NTCA phenylimide benzimidazole dye and produced 10.8 dye of formula VII, R=R'=H, n=2. The elemental analysis calculated for $C_{38}H_{15}N_3O_{11}S_2 \cdot 2(H_2O)$ was N 5.32; S 8.11. The elemental analysis determined was N 4.87, 4.90; S 8.45, 8.64.

The sulfonation procedure described in this example was repeated using AATCA ethoxyphenylimide chlorobenzimidazole dye (10 g) instead of NTCA phenylimide benzimidazole dye and produced 11.8 dye of formula VII, R=$C_2H_5O$, R'=Cl, n=2. The elemental analysis calculated for $C_{40}H_{18}ClN_3O_{12}S_2 \cdot 2(H_2O)$ was Cl, 4.08; N 4.83; S 7.36. The elemental analysis determined was Cl, 3.67, 3.90; N 4.34, 4.51.

The sulfonation procedure described in this example was repeated using AATCA 4-phenyloxyphenylimide benzimidazole dye (10 g) instead of NTCA phenylimide benzimidazole dye and produced 13.0 g dye of formula VII, R=OPh, R'=$CH_3$, n=3. The elemental analysis calculated for $C_{45}H_{21}N_3O_{15}S_3 \cdot 3(H_2O)$ was N 4.23; S 9.67. The elemental analysis determined was N 3.99, 4.27; S 9.45, 9.81.

EXAMPLE 5

Synthesis of a dye with formula VIII, X=S, R=$CH_3O$, M=$H^+$ was performed by the sulfonation procedure described below.

Dimethoxythioindigo (10 g) is dissolved in 18–25% oleum (50 ml) to form a reaction mixture. The reaction mixture is stored at room temperature for 15–18 hours until obtaining a water-soluble probe. (By "obtaining a water-soluble probe" is meant that 0.1 ml of the reaction mixture is diluted with 10 ml of water. When the reaction mixture dissolves in the water, a water-soluble probe is obtained.) Then, the reaction mixture is diluted with water to a sulfuric acid concentration of 50%, and 25 g sodium chloride is added. The resultant suspension is heated to 50° C. and filtered in the hot state. The residue is washed with a 15% solution of sodium chloride, then with 16% hydrochloric acid until no sulfate anions are detected in the filtrate. The filtrate is then dried. The dry residue is boiled in 100 ml of ethyl alcohol, hot filtered, washed with 20 ml ethyl alcohol, and dried to yield 12.4 g dye with formula VIII, R=$CH_3O$. The elemental analysis calculated for $C_{18}H_{12}O_{10}S_4 \cdot 4(H_2O)$ was S 21.81. The elemental analysis determined was S 21.77, 21.89.

The sulfonation procedure described in this example was repeated using dietoxythioindigo dye (10 g) instead of dimethoxythioindigo dye and produced 12.5 g dye of formula VIII, R=$C_2H_5O$. The elemental analysis calculated for $C_{20}H_{16}O_{10}S_4 \cdot 4(H_2O)$ was S 20.82. The elemental analysis determined was S 20.34, 20.42.

The sulfonation procedure described in this example was repeated using dichlorothioindigo dye (10 g) instead of dimethoxythioindigo dye and produced 10.5 g dye of formula V, R=Cl. The elemental analysis calculated for $C_{16}H_6Cl_2O_8S_4 \cdot 2(H_2O)$ was S 22.86; Cl, 12.64. The elemental analysis determined was S 22.26, 22.44; Cl, 12.09, 12.23.

The sulfonation procedure described in this example was repeated using dianizidinodichloropyrenequinone dye (10 g) instead of dimethoxythioindigo dye and produced 12.6 dye of formula XI, R=$CH_3O$, n=2. The elemental analysis calculated for $C_{30}H_{22}Cl_2N_2O_{10}S_2 \cdot 2(H_2O)$ was S 8.65; Cl, 9.58; N 3.78. The elemental analysis determined was S 8.33, 8.50; Cl, 10.05, 10.10; N 3.60, 3.68.

The sulfonation procedure described in this example was repeated using the di(methylphenylamino)-dichloropyrenequinone (5.0 g) yields a dye with formula XI, where R=$CH_3$. The elemental analysis calculated for $C_{30}H_{22}Cl_2N_2O_8S_2 \cdot 2(H_2O)$ was S 9.03; Cl 10.00; N 3.95. The elemental analysis determined was S 8.67, 9.12; Cl 9.95, 10.68; N 3.60, 3.81.

The sulfonation procedure described in this example was repeated using 2-phenyl-6-(4-methylphenyl)-aminopyrimidanthrone dye (10 g) instead of dimethoxythioindigo dye and produced 12.0 g dye of formula XIV: R=Ph, R'=$CH_3$, X=H, n=2. The elemental analysis calculated for $C_{26}H19 30_7S_2 \cdot 2(H_2O)$ was N 7.04; S 10.72. The elemental analysis determined was N 6.66, 6.89; S 10.78, 10.90.

The sulfonation procedure described in this example was repeated using 4-bromo-6-(4'-phenylamino) anilinepyrimideanthrone dye (10 g) instead of dimethoxythioindigo dye and produced 11.8 g dye of formula XIV, R=H, R'=$NHC_6H_5$, X=Br, n=2. The elemental analysis calculated for $C_{26}H_{17}BrN_4O_7S_2 \cdot 2(H_2O)$ was Br 11.82; N 8.27; S 9.45. The elemental analysis determined was Br, 11.78, 11.78; N 7.98, 8.30; S 8.97, 9.20.

The sulfonation procedure described in this example was repeated using 2-phenyl-6-(4'-phenyloxy) anilinpyrimideanthrone dye (10 g) instead of dimethoxythioindigo dye and produced 10.8 g dye of formula XIV, R=$C_6H_5$, R'=$OC_6H_5$, X=H, n=3. The elemental analysis calculated for $C_{32}H_{21}N_3O_{11}S_3 \cdot 3(H_2O)$ was N 5.43; S 12.42. The elemental analysis determined was N 5.01, 5.33; S 11.90, 12.25.

The sulfonation procedure described in this example was repeated using 2-(4'-chlorphenyl)-6-(4'-phenyloxy)

anilinpyrimideanthrone-4-sulfonic acid dye (10 g) instead of dimethoxythioindigo dye and produced 9.8 g dye of formula XIV, R=ClC$_6$H$_4$, R=OC$_6$H$_5$, X=SO$_3$H, n=2. The elemental analysis calculated for C$_{32}$H$_{20}$ClN$_3$O$_{11}$S$_3$.3(H$_2$O) was Cl 4.39; N 5.20; S 11.89. The elemental analysis determined was Cl 4.00, 4.34; N 4.90, 5.11; S 11.78, 11.98.

EXAMPLE 6

Synthesis of dyes with formula XV was performed by the method described in Inventor' Certificate no. 765 325, Cl. C09B 1/28, published 1980, using the corresponding derivatives of 1-amino-4-bromoanthraquinone.

EXAMPLE 7

Synthesis of a dye with formula XVI, R'=R"=CH$_3$, n=2, A-=CH$_3$SO$_4$ was performed as described below. A solution of 1,4-diaminoanthraquinone-2,3-dicarboxylic anhydride (3.08 g) and dimethylaminoethylamine (1.32 g) in acetic acid (30 ml) is heated to boiling and boiled for 4 hours to form a reaction mixture. Then, the reaction mixture is cooled, and the resultant precipitate is filtered, washed with ethyl alcohol, and dried to yield 3.6 g of 1,4-diaminoanthraquinone-2,3-dicarboxylic acid dimethylaminoethylimide.

The imide is suspended in 100 ml of chlorobenzene, mixed at room temperature with a solution of 0.5 ml dimethylsulfate in 10 ml chlorobenzene, stirred for 5 hours, and held overnight. Then the precipitate is filtered, washed with benzene and petroleum ether, and dried to yield 4.85 g of dye.

A similar reaction with 3-diethylaminopropylamine yields a dye with formula XVI, R'=C$_2$H$_5$, R"=CH$_3$, Y=CH$_3$SO$_4$ or Cl.

The synthesis of azo dyes with formula XVII is performed by a standard method (see, e.g., Chalykh, E. A., et al., Anilinokras. Prom-st', 1976, no. 10, p. 8; Ibid, 1977, no. 4, p. 31.) based on the reaction of azocombination between the corresponding salts of diazonium and phenylaminoethylalkyldimethylammonium synthesized as described in Inventor' Certificate No. 280 486, Cl. 707C 87/00, published 1970. synthesized as described in Inventor' Certificate No. 280 486, Cl. 707C 87/00, published 1970.

The synthesis of dyes with formula XVIII is performed by the conventional method described in Chalykh, E. A., et al., Anilinokras. Prom-st', 1976, no. 10, p. 8; Ibid, 1977, no. 4, p. 31.

Dyes with formula XIX are obtained using the known method described in Nikolenko, L. N., Laboratornyi Praktikum po Promezhutochnym Produktam i Krasitelyam (Laboratory Practical Training in Semiproducts and Dyes), Moscow, 1961, pp. 222–223.

Azodyes with formula XX are synthesized as described in Inventor' Certificate No. 226 756, Cl. 22a, 1, published 1968.

EXAMPLE 8

Synthesis of a dye with formula XXIIa, R'=H, Y=H was performed as described below.

A mixture of 1,1'-binaphthyl-4,4',5,5'-tetracarboxylic acid (BTCA) dianhydride (39.4 g or 0.1 mol) para-phenylenediamine (12.96 g or 0.12 mol), and sodium acetate (8.2 g) in 300 ml dimethylacetamide (DMAA) or dimethylsulfoxide (DMSO) is heated at 100–120° C. for 12 hours to form a reaction mixture. Then, the reaction mixture is poured into a mixture of 1000 ml water and 100 ml concentrated hydrochloric acid. The resultant precipitate is filtered, washed with water and dried. Dye yield was 45.2 g (95.8%).

EXAMPLE 9

Dye XXIIa with R'=COOH, (i.e. M=H$^+$), Y=H was obtained by the procedure described in Example 8 with the following exception. In the condensation reaction, 1,1'-binaphthyl-4,4',5,5',8,8'-hexacarboxylic acid (BHCA) dianhydride was used to replace 1,1'-binaphthyl- 4,4',5,5'-tetracarboxylic acid (BTCA) dianhydride using the same molar ratio of the reagents.

EXAMPLE 10

A dye with formula XXIIb, R'=NO$_2$, Y=H was obtained by condensation of 8,8'-dinitro-BTCA dianhydride with benzidine in acetic acid according to the procedure described in Example 8 using the same molar ratio of reagents as in that example.

EXAMPLE 11

Synthesis of a dye with formula XXIIc, R'=SO$_3$H, (i.e. M=H+), X=O, Y=H was performed as described below.

A mixture of 8,8'-disulfo-BTCA dianhydride (5.54 g or 0.01 mol), 4,4'-diaminodiphenyl ether (2.38 g or 0.012 mol), and sodium acetate (0.82 g) in 100 ml water is heated at 100–105° C. for 10 hours, cooled, acidified to pH 1.0, and filtered. The residue is pressed, and washed with water until the filtrate has a neutral pH. Dye yield 7.02 g (93.8%).

EXAMPLE 12

A dye with formula XXIIc, R'=SO$_3$H, X=CH=CH, Y=SO$_3$H was obtained by condensation of 8,8'-disulfo-BTCA dianhydride with 4,4'-diaminostilbene-2,2'-disulfo acid according to the procedure of Example 11.

EXAMPLE 13

A dye with formula XXIIb, R'=COOH, Y=COOH was obtained by condensation of BHCA dianhydride with benzidine-3,3'-dicarboxylic acid as described in Example 10.

EXAMPLE 14

A dye with formula XXIIb, R'=COOH, Y=CH$_3$O was obtained by condensation of BHCA dianhydride (0.1 mol) with dianizidine (0.12 mol) as described in Example 10.

EXAMPLE 15

A dye with formula XXIIc, R'=COOH, X=CONH, Y=H was obtained by condensation of BHCA dianhydride (0.1 mol) with 4,4'-diaminobenzanilide (0.12 mol) as described in Example 8.

EXAMPLE 16

A dye with formula XXIIb, R'=H, Y=CH$_3$ was obtained by condensation of BTCA dianhydride (0.1 mol) with 3,3'-tolidine (0.12 mol) as described in Example 10.

EXAMPLE 17

A dye with formula XXIIc, R'=SO$_3$H, X=NH, Y=H and SO$_3$H was obtained by condensation of 8,8'-disulfo-BTCA dianhydride (0.01 mol) with 4,4'-diaminodiphenylamine-2-sulfo acid (0.012 mol) as described in Example 11.

EXAMPLE 18

A dye of formula XXIIc, R'=COOH, X=NHCONH, Y=H was obtained by condensation of BHCA dianhydride (0.1 mol) with 4,4'-diaminodiphenylurea (0.12 mol) as described in Example 8.

EXAMPLE 19

Synthesis of dyes with general formula XXIII (R'=H, $NO_2$, COOM, $SO_3M$) were prepared according to the general procedure described below.

A mixture of 8,8'-disubstituted-BTCA dianhydride (0.01 mol), tetraaminodiphenyl ether (0.01 mol), and sodium acetate (0.8 g) in 100 ml dimethylsulfoxide is heated at 100–110° C. for 10–15 hours to form a reaction mixture. After termination of the reaction (as monitored by the absence of 8,8'-disubstituted-BTCA dianhydride in layer chromatography on plates with a fixed layer of silica gel), the reaction mixture is poured into a mixture of 1000 ml water and 100 ml of concentrated hydrochloric acid. The resultant precipitate is filtered, washed with water, and dried. Dye of formula XXIII yield ranged from 85–90%

EXAMPLE 20

Synthesis of dyes with formula XXIV were prepared according to the general procedure described below. In this example, the atomatic diamine was changed to obtain different variants of the formula:

p-phenylenediamine—a dye of formula XXIV, R=a), Y=H;
4,4'-diaminodiphenylether—a dye of formula XXIV, R=c, X=O; Y=H;
benzidine—a dye of formula XXIV, R=b, Y=H.

A mixture of 1,4,5,8-naphthalinetetracarboxylic acid (NTCA) dianhydride (0.01 mol) and the corresponding aromatic diamine (0.01 mol) in 100 ml of polyphosphoric acid is heated at 200° C. for 25 hours to form a reaction mixture. Then the reaction mixture is cooled to 70–90° C. and poured in a thin stream into 500 g of crushed ice. The precipitate is filtered, washed with water, and dried. Dye yield 90–95%.

EXAMPLE 21

A dye of formula XXV, Y=H was obtained by condensation of NTCA dianhydride with tetraaminodiphenyl ether as described in Example 19.

EXAMPLE 22

Synthesis of a dye with formula XXV, Y=$SO_3H$ was performed as described below.

Dye XXV with Y=H (5.0 g) (prepared as described in Example 21) is dissolved in 20% oleum (50 ml), heated to 85–90° C., and maintained at this temperature for 5 hours until obtaining a water soluble probe. The reaction mixture is cooled to room temperature and then 90 ml of water is added dropwise, with the simultaneous cooling on an ice bath to maintain the reaction mixture at a temperature that does not exceed 35–40° C. After stirring the mixture for 30 minutes, the reaction mixture is filtered and the residue is washed sequentially with 55% and 40% sulfuric acid. The final residue is washed with 15% hydrochloric acid and dried. Dye yield 6.46 g (93.8%).

EXAMPLE 23

Synthesis of dyes with formula XXVI were prepared according to the general procedure described below. 9.0 g sodium dithionite is added to a solution of a dye with formula XXII, R'=COOH (prepared as described in Example 9) (3.6 g) in 300 ml of 2% sodium hydroxide to form a reaction mixture. The reaction mixture is heated to 80–85° C. and maintained at this temperature for 30 minutes. Then the resultant violet reaction mixture is bubbled with air until a red precipitate is formed. The red precipitate is filtered, washed with water and dried. Dye yield, 65–80%.

The above procedure was repeated changing the starting dye as follows:

From the dye of formula XXII, R=a), Y=H; a dye of formula XXVI, R=a), Y=H was prepared.

From the dye of formula XXII, R=b), Y=H; a dye of formula XXVI, R=b), Y=H was prepared.

From the dye of formula XXII, R=c), X=O, Y=H; a dye of formula XXVI, R=c), X=O, Y=H—was prepared.

From the dye of formula XXII, R=c), X=NH, Y=$SO_3M$, M=$Na^+$; a dye of formula XXVI, , R=c), X=NH, Y=$SO_3M$, M=$Na^+$—was prepared.

EXAMPLE 24

Synthesis of a dye of formula XXVII, Y=H was performed as described below.

2.5 g sodium hydroxymethylsulfinate is added to a solution of a dye with formula XXIII, R'=COOH (prepared as described in Example 19) (5.2 g) in 500 ml of 2% sodium hydroxide to form a reaction mixture. The reaction mixture is heated to 96–98° C. and maintained at this temperature for 30 minutes. Then, the resultant blue-violet reaction mixture is bubbled with air until excess reducer agent is removed and a blue precipitate is formed. The precipitate is filtered, washed with water and dried. Dye yield, 3.9 g (88%).

EXAMPLE 25

Synthesis of a dye with formula XXVII, Y=$SO_3H$ was performed as described below.

Dye XXVII with Y=H (prepared as described in Example 24) (2.5 g) is dissolved in 20% oleum (10 ml), mixed with 5 ml chlorosulfonic acid, heated to 85–90° C., and maintained at this temperature for 8–10 hours until obtaining a water-soluble probe. Then, the reaction mixture is cooled and 30 ml water is added dropwise while the temperature of the reaction mixture is maintained at or below 40° C. After stirring the reaction mixture for 30 minutes at room temperature, the reaction mixture is filtered. The residue is pressed, washed with 20% hydrochloric acid until no sulfate anions are detected in the filtrate (as determined by barium chloride) and dried. Dye yield 2.8 g (88%).

EXAMPLE 26

Dyes with formulas XXVIII and XXIX, Y=H were prepared as described below.

Dye XXII (prepared as described in 9, 13–15, 18) or XXIII (prepared as described in Example 19) with R'=COOH (0.01 mol) is dissolved in 95–98% sulfuric acid (100 ml), heated to 120–125° C., and maintained at this temperature for 2–3 hours. Then, the reaction mixture is cooled and diluted with 500 ml water. The precipitate is filtered, washed with water, and dried. Dye yield 95–97%.

EXAMPLE 27

According to the method of Example 25, a dye with formula XXIX, Y=$SO_3H$ was obtained by sulfonation of the corresponding dye XXIX, Y=H (prepared as described in Example 26).

EXAMPLE 28

Dyes with formulas XXX were prepared as described below. Following this procedure when p-phenylenediamine was used as the bis-diamine and H-acid as azo-component, a dye of formula XXX, R=a), R'=OH, R"=$NH_2$, Y=H, M=$NH_4^+$ was prepared. When benzidine and chromotropic acid were used, a dye of formula XXX, R=b), R', R"=OH, Y=H, M=$NH_4^+$ was prepared.

(a) Diazotization of bis-diamine. The corresponding bis-diamine (0.05 mol) is dissolved in a mixture of water (100 ml) and 30% hydrochloric acid (30 ml) to form a reaction mixture. The reaction mixture is cooled on ice to 0° C. Then 0.1 mol of sodium nitrite is added in the form of a 30% solution, and the reaction mixture is stirred for 1 hour.

(b) About 1–2 hours before the reaction, a solution of the azo component is prepared by dissolving 0.05 mol of an H- or chromotropic acid (the dye intermediate) in 100 ml water in the presence of sodium carbonate to form a reaction mixture. The reaction mixture is cooled to 6–8° C., poured slowly (over a period of about 1 hour) at this temperature into a solution of diazo compound, and stirred for 1–2 hours. Then the reaction mixture is alkalized by adding 10 ml of 40% sodium hydrochloride, mixed with 10 g of sodium carbonate, cooled by adding ice to the reaction mixture and placing the reaction mixture in an ice bath to a temperature of 2–4° C., and stirred for 4–6 hours. The reaction is terminated after 4–6 hours of stirring, 150 ml of isopropanol and 100 ml of saturated ammonium bicarbonate are added and the mixture is stored for 3–5 hours. The resultant precipitate is filtered and washed with 100 ml of saturated ammonium bicarbonate. The dye product is dried at 80–100° C.

EXAMPLE 29

Synthesis of a dye with formulas XXXI, A=a, b, c was performed as described below.

A mixture of the corresponding dichloroanthraquinone (0.01 mol), aromatic diamine (0.01 mol), and copper acetate (1.0 g) in 25 ml nitrobenzene is heated at 170–180° C. for 15 hours to form a reaction mixture. Then the reaction mixture is cooled, and the resultant precipitate is filtered, washed with 25 ml ethanol, pressed, and cooked to a pulp by boiling with 5% hydrochloric acid (100 ml). The reaction mixture is filtered, and the precipitate is washed with water until the filtrate is a neutral pH, and dried. Dye yield, 88–95%.

EXAMPLE 30

Synthesis of a dyes with formula XXXI, R=b, A=d was performed as described below.

A mixture of 2,7-dibromoanthanthrone (0.01 mol), aromatic diamine (0.01 mol), benzidine (0.01 mol), copper oxide (1.0 g), and 1.5 sodium carbonate is placed in 30 ml nitrobenzene and heated at 200–205° C. for 12–18 hours. Then the reaction mixture is cooled and the resultant precipitate is filtered, washed with 3 portions of acetic acid (10 ml each), pressed, and cooked to a pulp by boiling with 5% hydrochloric acid (100 ml). The reaction mixture is cooled and filtered. The precipitate is washed with water and dried. A dye of formula XXXI, A=d, R=b, Y=H was obtained.

EXAMPLE 31

A dye with formula XXXI, A=e, R=a, Y=H was obtained by condensation of 3,9-dibromobenzanthrone with the p-phenylenediamine according to the procedure of Example 30.

EXAMPLE 32

A dye with formula XXXI, A=f, R=c, X=NH, Y=H was obtained by condensation of tetrachloropyrenequinone with 4,4'-diaminodiphenylamine according to the procedure of Example 30.

EXAMPLE 33

A dye with formula XXXI, A=g, R=C, X=O, Y=H, was obtained by condensation of dibromoindigo with 4,4'-diaminodiphenylether according to the procedure of Example 30.

EXAMPLE 34

Conversion of polymeric dyes with formulas XXII–XXXI into a water-soluble form was performed as described below. Method 1 A polymeric dye of the type XXII–XXIV is dissolved in 20 ml monohydrate, the solution is heated to 50° C., and maintained at this temperature for 5–15 hours until obtaining a water-soluble probe. The reaction is then terminated and the sulfided reaction mixture is diluted with 40 ml of water. The resultant precipitate is filtered, washed sequentially with 17.5% and 5% hydrochloric acid until no sulfate anions are present in the filtrate (as determined by barium chloride). The dye is purified by reprecipitation from water with a mixture of isopropanol and saturated ammonium bicarbonate solution.

Method 2

A polymeric dye of the type XXV–XXIX is dissolved in 10 ml of 10–20% oleum, mixed with 10 ml of chlorosulfonic acid, and heated at 70–80° C. for 7–8 hours until obtaining a water-soluble probe. The reaction is terminated and the sulfonated material is diluted with 50 ml of water. The resultant precipitate is filtered, washed sequentially with concentrated, 17.5%, and 5% hydrochloric acid until no A polymeric dye of the type XXXI or XXXII is dissolved in 20 ml of 20–25% oleum and heated at 85–90° C. for 0–12 hours until obtaining a water-soluble probe. The reaction is terminated and the sulfonated material is diluted with 50 ml of water. The precipitate is filtered, washed sequentially with concentrated, 17.5%, and 5% hydrochloric acid until no sulfate anions are present in the filtrate (as determined by barium chloride). The dye is purified by reprecipitation from water with a mixture of isopropanol and saturated ammonium carbonate solution.

EXAMPLE 35

A dye with formula XXXIII, R'=H, X=NH, R=$C_6H_4$, A=a was prepared as described below.

1.35 g acrylic acid chloroanhydride is added to a solution of 3.5 g 1-amino-4-(4'-aminophenyl)aminoanthraquinone in 25 ml ortho-dichlorobenzene to form a reaction mixture, and the reaction mixture is heated at 85–90° C. for 3 hours. The reaction mass is cooled, mixed with 25 ml petroleum ether, and stirred at room temperature for 25 minutes. The resultant precipitate is filtered, washed with petroleum ether, and dried. The resultant acyl derivative is dissolved in 30 ml dimethylformamide to form a reaction mixture. Then 0.025 g ammonium persulfate is added to the reaction mixture. The reaction mixture is bubbled with nitrogen for 30 minutes, and heated at 80° C. for 4 hours. The reaction mixture is diluted with 300 ml of water. The resultant precipitate is filtered, washed with water and methanol, and dried. Dye yield, 4.6 g (98%).

EXAMPLE 36

A dye with formula XXXIII, R'=$CH_3$, X=O, R=b for Y=H of formula XXII, A=e was obtained as described in Example 33. However, instead of 1-amino-4-(4'-aminophenyl)-aminoanthraquinone, 4-(4'-aminophenyl)phenylimide 1,4-diaminoanthraquinone-2,3-dicarboxylic acid was used.

EXAMPLE 37

A dye with formula XXXIII, R°=H, X=NH, R=$(CH_2)_3$, A=c was obtained as described in Example 33. However, aminopropylimide 1,4-diaminoanthraquinone 2,3-dicarboxylic acid was used instead of 1-amino-4-(4'-aminophenyl)-aminoanthraquinone.

EXAMPLE 38

A dye with formula XXXIII, R'=$CH_3$, X=NH, A=d, $R^3$=H or Br was obtained as described in Example 33. However, 2-phenyl-4-bromo-6-(4'-aminophenyl)-aminopyrimidanthrone was used instead of 1-amino-4-(4'-aminophenyl)-aminoanthraquinone.

EXAMPLE 39

A dye with formula XXXIII, $R_o=CH_3$, X=NH, R as in formula XXII was obtained as described below.

1.5 g methacrylic acid chloroanhydride is added to a solution of 0.01 mol 1-amino-4-(para-aminoaryl)-aminoanthraquinone in 25 ml dimethylsulfoxide to form a reaction mixture, and the reaction mixture is heated at 45–50° C. for 2 hours. The reaction mixture is poured into 300 ml of it hydrochloric acid. The resultant precipitate is filtered, washed with water and dried. The resultant monomeric dye is stirred in 30 ml of distilled water under nitrogen flow, mixed with 0.1 potassium persulfate in 4 ml distilled water, and heated at 80° C. for 2 hours to form a reaction mixture. 70 ml acetone is added to the reaction mixture and the precipitate is filtered, washed with acetone and petroleum ether, and dried. The dye is obtained with a quantitative yield.

EXAMPLE 40

A dye with formula XXXIII, $R^o=CH_3$, A=e, X=O, was obtained as described in Example 39 using N,N'-bis[4(4-hydroxy-3-carboxyphenylazo)phenyl]urea instead of 1-amino-4-(para-aminoaryl)aminoanthraquinone.

EXAMPLE 41

Dyes with formula XXXII were obtained by copolycondensation of NTCA and PTCA dianhydrides and dihalide derivatives of polycyclic compounds with aromatic diamines using quinoline as the solvent as described in Example 30. All the other dyes of formula XXXII were obtained in the same manner.

EXAMPLE 42

A dye with formula XXXIV, $R^o=H$; A=a where R=H; $R'=C_6H_4-O-C_6H_4$; X'=NH; B=d where $R^o=X=H$; $R'=C_6H_4-NH-C_6H_4$; X=NH; D=f where $R=COC_6H_5$; $R''=C_6H_4$; X''=NH was obtained by copolymerization of three monomeric dyes. The mixture of 2.38 g (0.005 mol) 1-amino-4-[4-(p-acryloylaminophenyloxy)phenyl]-aminoanthraquinone, 2.8 g (0.005 mol) 2-phenyl-6-[4-(p-N-acryloylaminophenylamino)phenyl] aminopyrimideanthrone, and 2.44 g (0.005 mol) 1-benzoylamino-5-(p-N-acryloylaminophenyl) aminoanthraquinone is dissolved in 100 ml dimethylformamide to form a reaction mixture. Then 0.025 g ammonium persulfate is added to the reaction mixture. The reaction mixture is bubbled with nitrogen for 30 minutes, and heated at 80° C. for 4 hours. The reaction mixture is diluted with 500 ml of water. The resultant precipitate is filtered, washed with water and methanol, and dried. Dye yield, 7.1 g (93%).

EXAMPLE 43

Characteristics of polarization coatings prepared using the above materials are summarized in the Table. According to these data, these materials were used to prepare yellow, red, green, and, particularly, grey DLPs with high polarization properties ($K_d>15$). Thus, data presented in the table show that the liquid crystal material provides polarization characteristics of DLPs to be improved ($K_d>15$) as compared to the prototype ($K_d=7–10$). Therefore, dichroic light polarizers based on these materials can be employed not only in the automotive industry and architecture, but in the production of recording and display devices using high resolution liquid crystal matrices.

Compositions for the production of polarizing coating and the polarization properties of DLPs

| # | Dye | Solvent | Inhibitor, antioxidant | Surfactant | Modif. agent | Characteristic Color | $K_d$ |
|---|---|---|---|---|---|---|---|
| 1 | I, R = H, n = 21 10% | water | Hydroquinone, 0.1% | Triton X-100 1% | Polyethylene glycol 5% | yellow | 17.0 |
| 2 | II, n = 3 7% | water + ethanol | — | Sodium dodecil sulphate 0.1% | Lacquer KO 10% | yellow | 20.9 |
| 3 | III, n = 4 R = NCOPh 20% | water | — | — | Polyethylene glycol 15% | orange | 19.0 |
| 4 | IV, R = H, n = 2 10% | Water | — | Triton X-100 5% | Pentaerythritol 20% | orange | 17.8 |
| 5 | V, R = NHPh, R' = H, n = 4 25% | Water + isopropyl alcohol | phenylglycine 1% | — | Polyethylene glycol 10% | yellow | 23.0 |
| 6 | V, R = $OCH_3$ R' = $CH_3$ n = 2 30% | Water | — | Triton X-100 10% | 0.1% | Yellow | 20.6 |
| 7 | VI, R = R' = H, n = 2 15% | Water + dioxane | — | — | Poly acrylamide 2% | Red dish-violet | 18.8 |
| 8 | VIII, X = S R = Cl, n = 2 25% | Water | Pyrocatechin | — | Polyethylene imide 0.5% | Pink | 15.7 |
| 9 | X, R = $OCH_3$ n = 2 | Water + buthanol | — | Sodium perfluoro | Succinic aldehyde | Green | 16.8 |

-continued

Compositions for the production of polarizing coating and the polarization properties of DLPs

| # | Dye | Solvent | Inhibitor, antioxidant | Surfactant | Modif. agent | Characteristic Color | $K_d$ |
|---|---|---|---|---|---|---|---|
| | 8% | | | octanoate 0.5% | 5% | | |
| 10 | XI, R = OPh, n = 4 15% | Water | Hydro quinone, 1% | Poly vinyl alcohol 2% | Polyethylene glycol 5% | Green | 21.5 |
| 11 | XII, R = H, n = 2 10% | Water + acetone | — | — | Polyethylene glycol 8% | Olive | 22.6 |
| 12 | XIV, R = Ph, R' = NHPh, X = Br, n = 3 10% | Water | — | Pentol 0.5% | POly phosphoric acid 10% | Red | 19.5 |
| 13 | XV, R = CH$_3$, R' = R" = CH$_3$, A = Cl, n = 2 10% | Water | — | Amido betaine 0.1% | Polyethylene glycol 10% | Blue | 18.7 |
| 14 | XVI, R = Et, R' = R" = CH$_3$, A = Br, n = 3 8% | Water + ethyl cello solve | — | — | Poly acrylamide 1% | Light- blue | 22.5 |
| 15 | XVII, R = CH$_3$, R' = R" = C$_2$H$_5$, A = I, X' = X" = X"' = Cl 7% | — | — | — | Polyethylene glycol 10% | Red | 18.6 |
| 16 | XXI, 10% | Water | Hydro quinone, 1% | Pentol 0.1% | Polyethylene glycol 5% | Red | 30.5 |
| 17 | XXV, Y = H 5% | Monohyd rate | — | — | Poly(p-benzoamide) 1% | Reddish | 29.5 |
| 18 | XXVII, Y = SO$_3$H 3% | Water | — | — | Sodium carbomethyl cellulose 1% | Blue | 30.6 |
| 19 | XXVII, R = a), 3% | Monohyd rate | — | — | Poly(p-benzoamide) 1% | Gray | 33.0 |
| 20 | Prototype - Dichroic light polarizer based on direct yellow light-resistant O dye | | | | | Yellow | 10.0 |
| 21 | Prototype with additive | | | | Sodium carbo methyl cellulose 5% | Yellow | 18.0 |
| 22 | Prototype - Dichroic light polarizer based on 3,4,9,10-perylenetetracarboxylic acid (PTCA) dimethyldiphenyldiimide disulfonic acid | | | | | Red | 12.0 |
| 23 | Prototype with additive | | | | Polyethylene glycol 5% | Red | |
| 24 | Prototype - Dichroic light polarizer based on 3,4,9,10-anthanthronetetracarboxylic acid (AATCA) dibenzimidazole disulfonic acid | | | | | Gray | 15.0 |
| 25 | Prototype with additive | | | | Polyethylene glycol 3% | Gray | 15.0 |

What is claimed is:

1. A dichroic light polarizer comprising a dye of a formula selected from the group consisting of I—XX and XXII—XXXIV, the dye comprising molecules aggregated into particles oriented in a predetermined direction on a surface of a substrate to enable the dye to polarize light transmitted through the dye.

2. The dichroic light polarizer of claim 1 comprising a dye of a formula selected from the group consisting of I—XXXIV, or mixtures thereof, and a modifying additive.

3. The dichroic light polarizer of claim 1 wherein the polarizing elements have differing orientations of the polarization vector in the substrate plane.

4. The dichroic light polarizer of claim 1 wherein the polarizing elements have differing colors.

5. The dichroic light polarizer of claim 1 wherein the dichroic light polarizer contains one or more additional molecularly oriented layers of an organic dye present on the layer of dye on the substrate surface.

6. The dichroic light polarizer of claim 5 wherein each additional dye layer contains different polarizing elements.

7. The dichroic light polarizer of claim 6 wherein the different polarizing elements of different layers have the same orientation of the polarization vector.

8. The dichroic light polarizer of claim 6 wherein the different polarizing elements of different layers have different orientations of the polarization vector.

9. The dichroic light polarizer of claim 6 wherein the different polarizing elements of different layers have the same color.

10. The dichroic light polarizer of claim 6 wherein the different polarizing elements of different layers have a different color.

11. The dichroic light polarizer of claim 5 wherein a layer of an optically transparent material is intermediate the dye layers.

12. The dichroic light polarizer of claim 1 wherein the polarizing elements have the shape of bands.

13. The dichroic light polarizer of claim 12 wherein the bands are of equal width.

14. The dichroic light polarizer of claim 12 wherein the bands are of different colors.

15. The dichroic light polarizer of claim 14 wherein the bands have parallel orientations of their polarization axes.

16. The dichroic light polarizer of claim 14 wherein the bands have perpendicular orientations of their polarization axes.

17. The dichroic light polarizer of claim 1 wherein the polarizing elements have an arbitrary shape.

18. The dichroic light polarizer of claim 17 wherein the polarization axes of neighboring polarizing elements form an angle of from 0 to 90° with respect to each other.

19. The dichroic light polarizer of claim 18 wherein the polarizing elements have the different colors.

20. A method of making a dichroic light polarizer comprising:

a. coating a substrate with a solution of an organic dye occurring in the lyotropic liquid-crystal state in a solvent while simultaneously orienting the dye; and b. removing the solvent.

21. The method of claim 20 wherein the direction of orienting action during the dye film orientation forms an angle $\alpha$ wherein $0<\alpha<90°$ with the direction of substrate motion.

* * * * *

UNITED STATES PATENT AND TRADEMARK OFFICE
CERTIFICATE OF CORRECTION

PATENT NO.    : 6,049,428
DATED         : April 11, 2000
INVENTOR(S)   : Khan et al.

It is certified that error appears in the above-identified patent and that said Letters Patent is hereby corrected as shown below:

Column 41,
Lines 62-66, replace "I—XX and XXII—XXXIV, the dye comprising molecules aggregated into particles oriented in a predetermined direction on a surface of a substrate to enable the dye to polarize light transmitted through the dye" with the following chemical drawings and language:

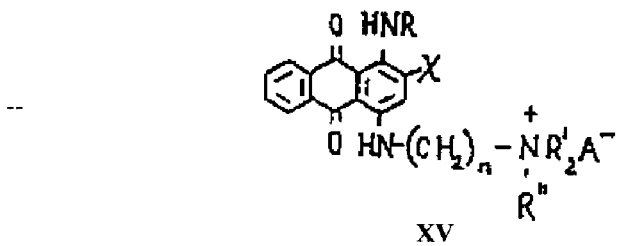

XV and

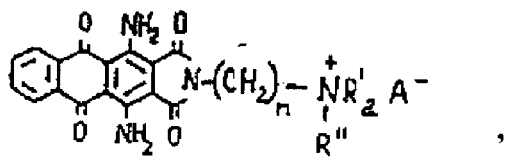

XVI wherein X is H or Br, R is selected from the group consisting of H, an alkyl group of 1-4 carbon atoms, and a substituted or unsubstituted phenyl radical, R' and R" are $CH_3$ or $C_2H_5$, $A^-$ is selected from the group consisting of a negative halide ion, $CH_3SO_4^-$, $ClO_4^-$, and $BF_4^-$, and n is 2 or 3;

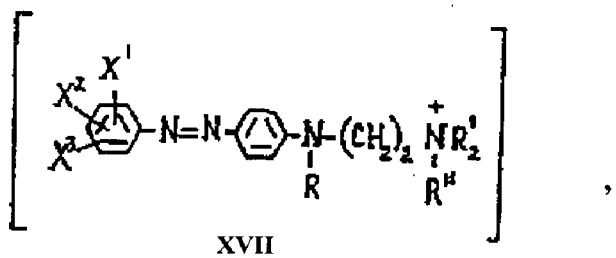

XVII wherein R is $CH_3$ or $C_2H_5$, R', R" and $A^-$ are defined as in formula XV, and $X^1$, $X^2$, and $X^3$ are selected from the group consisting of H, Cl, $NO_2$, and $CH_3O$;

UNITED STATES PATENT AND TRADEMARK OFFICE
CERTIFICATE OF CORRECTION

PATENT NO.   : 6,049,428
DATED        : April 11, 2000
INVENTOR(S)  : Khan et al.

It is certified that error appears in the above-identified patent and that said Letters Patent is hereby corrected as shown below:

Column 41 (cont'd),

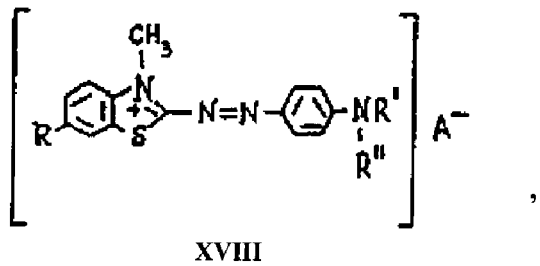

XVIII wherein R is H or $CH_3O$, R' is selected from the group consisting of $CH_3$, $C_2H_5$, and a substituted or unsubstituted phenyl radical, R" is $C_2H_5$ or $C_2H_4OH$; and $A^-$ is defined as in formula XV;

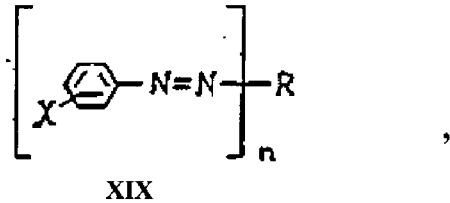

XIX wherein X is COOM or $PO(OM)_2$, wherein M is a cation, n is 1 or 2, and R =

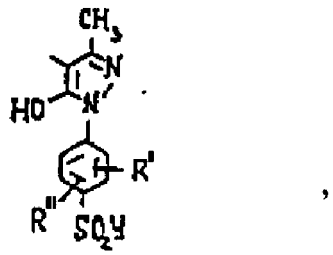

wherein Y is $NH_2$;

UNITED STATES PATENT AND TRADEMARK OFFICE
CERTIFICATE OF CORRECTION

PATENT NO. : 6,049,428
DATED : April 11, 2000
INVENTOR(S) : Khan et al.

It is certified that error appears in the above-identified patent and that said Letters Patent is hereby corrected as shown below:

Column 41 (cont'd),

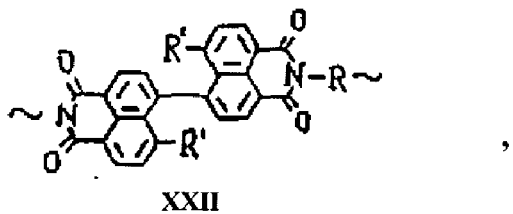

XXII wherein R' is selected from the group consisting of H, $NO_2$, and COOM, wherein M is a cation, and R =

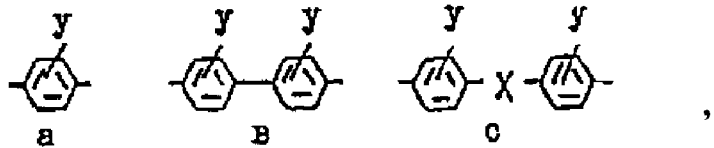

wherein X is selected from the group consisting of O, $CH_2$, NH, CONH, NHCONH, CH=CH, and Y is selected from the group consisting of H, $CH_3$, $CH_3O$, and COOM wherein M is a cation;

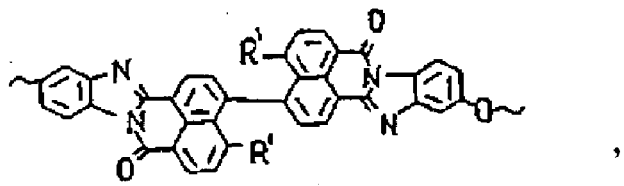

XXIII wherein R' is selected from the group consisting of H, $NO_2$, and COOM, wherein M is a cation;

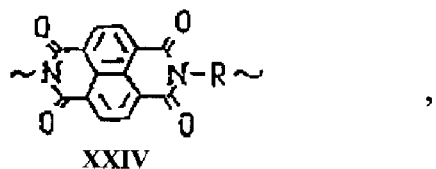

XXIV

UNITED STATES PATENT AND TRADEMARK OFFICE
CERTIFICATE OF CORRECTION

PATENT NO. : 6,049,428  
DATED : April 11, 2000  
INVENTOR(S) : Khan et al.

Page 4 of 8

It is certified that error appears in the above-identified patent and that said Letters Patent is hereby corrected as shown below:

Column 41 (cont'd),

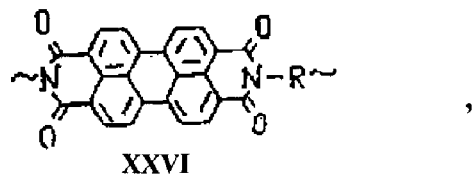

XXVI ,

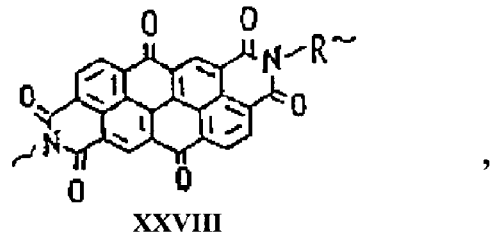

XXVIII ,

XXXI , and

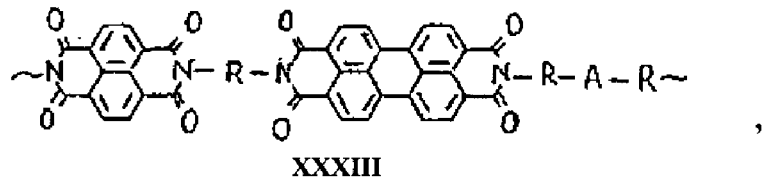

XXXIII wherein R is defined as in formula XXII, wherein Y is selected from the group consisting of H, CH₃, CH₃O, and COOM, and M is a cation, and A is selected from the group consisting of

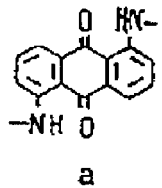   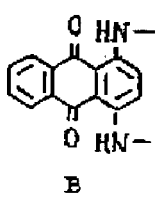   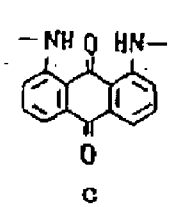

a          B          c

UNITED STATES PATENT AND TRADEMARK OFFICE
CERTIFICATE OF CORRECTION

PATENT NO. : 6,049,428
DATED : April 11, 2000
INVENTOR(S) : Khan et al.

It is certified that error appears in the above-identified patent and that said Letters Patent is hereby corrected as shown below:

Column 41 (cont'd),

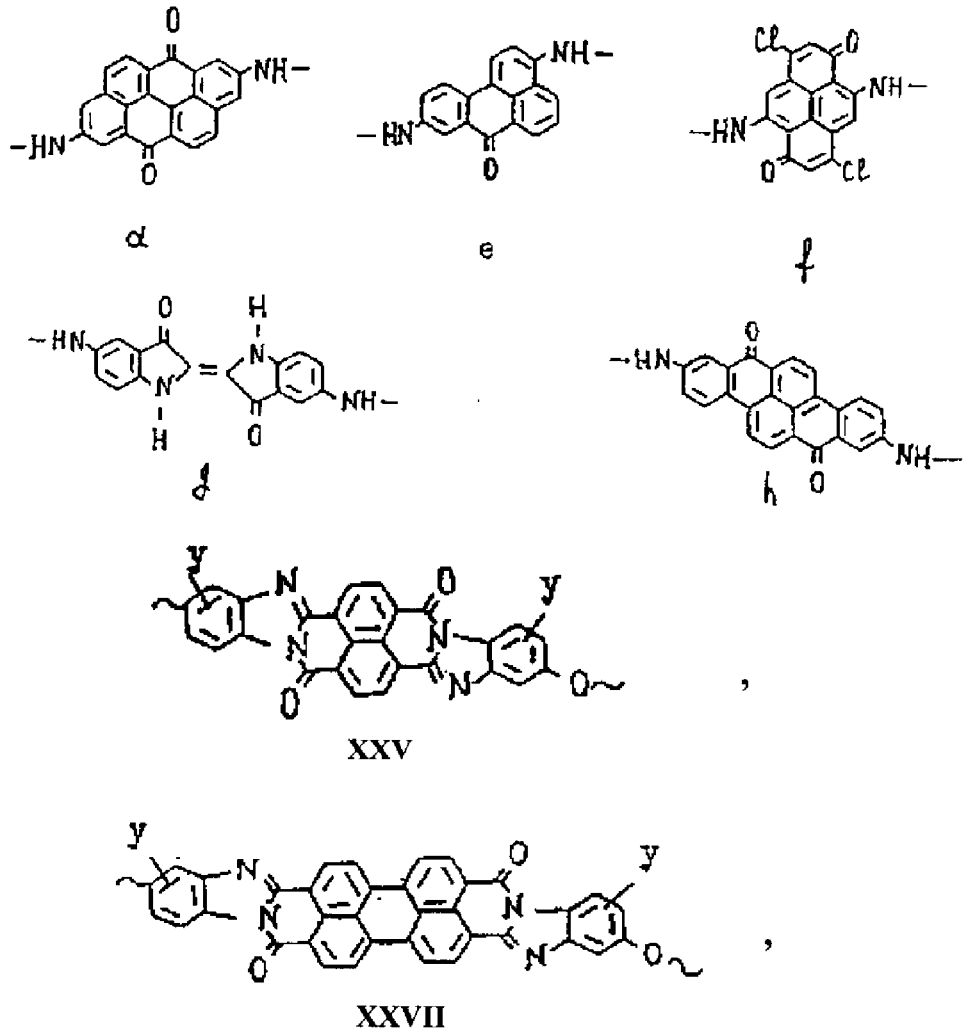

and

UNITED STATES PATENT AND TRADEMARK OFFICE
CERTIFICATE OF CORRECTION

PATENT NO. : 6,049,428
DATED : April 11, 2000
INVENTOR(S) : Khan et al.

It is certified that error appears in the above-identified patent and that said Letters Patent is hereby corrected as shown below:

Column 41 (cont'd),

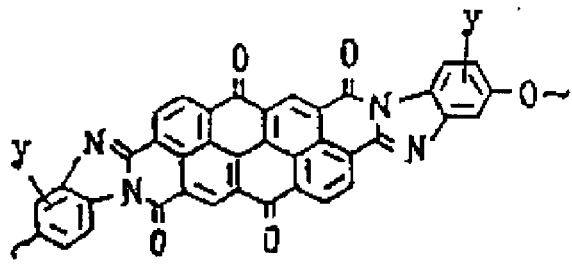

XXIX wherein Y is H; and

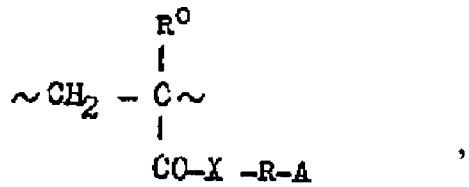

XXXIII wherein R is defined as in formula XXII or $(CH_2)_n$, wherein N is 3 or 6, $R°$ is H or $CH_3$, X is NH or O, and

A =

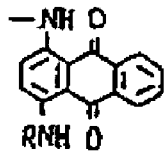  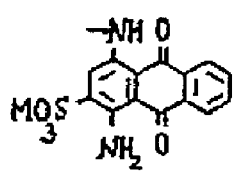  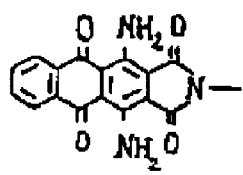

a            B            C

UNITED STATES PATENT AND TRADEMARK OFFICE
CERTIFICATE OF CORRECTION

PATENT NO.   : 6,049,428
DATED        : April 11, 2000
INVENTOR(S)  : Khan et al.

It is certified that error appears in the above-identified patent and that said Letters Patent is hereby corrected as shown below:

Column 41 (cont'd),

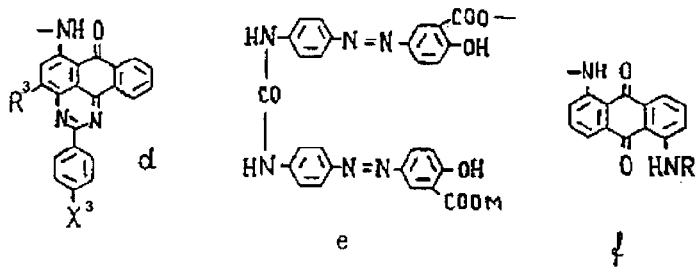

wherein $R^3$ is H or Br, and $X^3$ is H, and

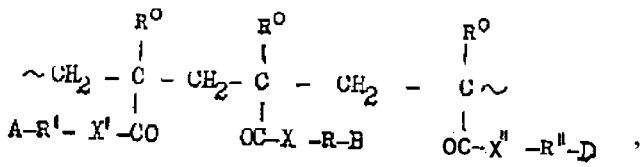

XXXIV

Wherein R, R' and R" are defined as R is formula XXXIII, $R°$ is defined as in formula XXXIII, X, X', and X" are defined as X is formula XXXIII, A, B, and D are defined as A is formula XXXIII, wherein $R^3$ and $X^3$ are defined as in formula XXXIII, Y is selected from the group consisting of H, $CH_3$, $CH_3O$, and COOM, wherein M is a cation, and A is selected from the group consisting of formulas a, c, e, and f in formula XXXIII;

the dye comprising molecules aggregated into particles oriented in a predetermined direction on a surface of a substrate to enable the dye to polarize light transmitted through the dye --.

Column 42,
Line 60, after the phrase "light polarizer of claim 1" insert -- further --.
Lines 60-62, delete the phrase "dye of a formula selected form the group consisting of I-XXXIV, or mixtures thereof, and".
Line 63, delete the phrase "wherein" and replace with -- comprising a molecularly oriented layer of an organic dye on a surface of a substrate wherein the layer has a non-periodic arrangement of different polarizing elements; --.
Line 64, replace the phrase "polarizing elements have" with -- polarizing elements having --.
Line 64, replace the phrase "orientations of the" with -- orientations of their --.
Line 65, replace the word "vector" with -- vectors --.
Line 66, replace the phrase "claim 1" with -- claim 3 --.

UNITED STATES PATENT AND TRADEMARK OFFICE
CERTIFICATE OF CORRECTION

PATENT NO. : 6,049,428
DATED : April 11, 2000
INVENTOR(S) : Khan et al.

It is certified that error appears in the above-identified patent and that said Letters Patent is hereby corrected as shown below:

Column 43,
Lines 1 and 22, replace the phrase "claim 1" with -- claim 3 --.

Column 44,
Line 6, replace the phrase "claim 1" with -- claim 3 --.

Signed and Sealed this

Fifteenth Day of February, 2005

JON W. DUDAS
*Director of the United States Patent and Trademark Office*